US008975598B2

(12) United States Patent
Rapoport et al.

(10) Patent No.: US 8,975,598 B2
(45) Date of Patent: Mar. 10, 2015

(54) ARTICLES INCORPORATING THERMOGRAPHIC PHOSPHORS, AND METHODS AND APPARATUS FOR AUTHENTICATING SUCH ARTICLES

(71) Applicant: Honeywell International Inc., Morristown, NJ (US)

(72) Inventors: William Ross Rapoport, Bridgewater, NJ (US); James Kane, Lawrenceville, NJ (US); Carsten Lau, Garbsen (DE); Chirag Patel, Bridgewater, NJ (US); Jack Steven Croiter, Brooklyn, NY (US)

(73) Assignee: Honeywell International Inc., Morristown, NJ (US)

( * ) Notice: Subject to any disclaimer, the term of this patent is extended or adjusted under 35 U.S.C. 154(b) by 120 days.

(21) Appl. No.: 13/737,594

(22) Filed: Jan. 9, 2013

(65) Prior Publication Data

US 2013/0181144 A1   Jul. 18, 2013

Related U.S. Application Data

(60) Provisional application No. 61/587,427, filed on Jan. 17, 2012.

(51) Int. Cl.
*G01J 1/58* (2006.01)
*G01N 21/64* (2006.01)
(Continued)

(52) U.S. Cl.
CPC ............ *G01N 21/64* (2013.01); *C09K 11/7701* (2013.01); *G01K 11/20* (2013.01);
(Continued)

(58) Field of Classification Search
CPC ......... G01K 11/20; G07D 7/00; G01N 25/00; G01N 21/64

USPC ........................................... 250/458.1, 459.1
See application file for complete search history.

(56) References Cited

U.S. PATENT DOCUMENTS 4,448,547 A * 5/1984 Wickersheim ................ 374/131
4,833,311 A * 5/1989 Jalon ............................. 235/491
(Continued)

FOREIGN PATENT DOCUMENTS

WO         2009136921 A1    11/2009
WO    WO 2011082794 A1 *   7/2011

OTHER PUBLICATIONS

International Search Report mailed Jun. 21, 2013 in International Application No. PCT/US2013/021417.
S.W. Allison, "Remote Thermometry With Thermographic Phosphors: Instrumentation and Applications", American Institute of Physics, Rev. Sci. Instrum. 68(7), Jul. 1997.
(Continued)

*Primary Examiner* — David Porta
*Assistant Examiner* — Jeremy S Valentiner
(74) *Attorney, Agent, or Firm* — Ingrassia Fisher & Lorenz PC

(57) ABSTRACT

Embodiments include methods and apparatus for identifying a thermographic phosphor (e.g., Er:YIG) incorporated on or within an article. The method and apparatus embodiments include an excitation energy generator selectively exposing the article to excitation energy in an absorption band of the thermographic phosphor. An emitted radiation detector detects first emission characteristics of first emitted radiation from the article within an emission band of the thermographic phosphor when the article has a first temperature, and detects second emission characteristics of second emitted radiation from the article within the emission band when the article has a second temperature that is different from the first temperature. A temperature adjustment element is configured to adjust the temperature of the article. Embodiments further include a processing system determining whether the first emission characteristics are sufficiently different from the second emission characteristics.

12 Claims, 6 Drawing Sheets

(51) Int. Cl.
*C09K 11/77* (2006.01)
*G01K 11/20* (2006.01)
*G01N 25/00* (2006.01)
*G07D 7/00* (2006.01)
*G07D 7/12* (2006.01)
*B42D 15/00* (2006.01)
*C09D 11/52* (2014.01)

(52) U.S. Cl.
CPC ............... *G01N 25/00* (2013.01); *G07D 7/00* (2013.01); *C09K 11/7769* (2013.01); *G07D 7/12* (2013.01); *G07D 7/122* (2013.01); *B42D 15/00* (2013.01); *C09D 11/52* (2013.01)
USPC ..................................... 250/459.1; 250/458.1

(56) References Cited

U.S. PATENT DOCUMENTS

| | | | |
|---|---|---|---|
| 5,110,216 A * | 5/1992 | Wickersheim et al. | 374/122 |
| 5,949,539 A | 9/1999 | Britton, Jr. et al. | |
| 6,365,904 B1 * | 4/2002 | Graves | 250/458.1 |
| 6,515,743 B1 * | 2/2003 | Hayashi et al. | 356/317 |
| 2002/0006153 A1 | 1/2002 | Ronson et al. | |
| 2009/0141961 A1 | 6/2009 | Smith et al. | |
| 2009/0159510 A1 | 6/2009 | Haushalter et al. | |
| 2010/0102250 A1 * | 4/2010 | Li et al. | 250/459.1 |
| 2012/0175528 A1 * | 7/2012 | Haubrich et al. | 250/459.1 |
| 2012/0256409 A1 * | 10/2012 | Giering et al. | 283/85 |

\* cited by examiner

ARTICLES INCORPORATING THERMOGRAPHIC PHOSPHORS, AND METHODS AND APPARATUS FOR AUTHENTICATING SUCH ARTICLES

PRIORITY CLAIMS

This application claims the benefit of U.S. Provisional Application No. 61/587,427, filed Jan. 17, 2012.

TECHNICAL FIELD

The present invention generally relates to radiation emitting compounds and methods and apparatus for their use as security materials.

BACKGROUND

A luminescent phosphor compound is a compound that is capable of emitting detectable quantities of radiation in the infrared, visible, and/or ultraviolet spectrums upon excitation of the compound by an external energy source. A typical luminescent phosphor compound includes at least a host material (e.g., a crystal lattice), an emitting ion (e.g., of a rare earth metal), and in some cases, a "sensitizing" ion (e.g., of a transition metal or of a different rare earth metal that can absorb and transfer the energy to the emitting rare earth metal ion). The production of radiation by a phosphor compound is accomplished by absorption of incident radiation by the emitting ion(s) or by either or both the host material and the sensitizing ion(s) followed by energy transfer from the host material/sensitizing ion(s) to the emitting ion(s), and radiation of the transferred energy by the emitting ion(s).

The selected components of a phosphor compound may cause the compound to have particular emission properties, including specific wavelengths for its excitation energy, and specific spectral position(s) for higher spectral energy output emitted by the emitting ions of the phosphor compound ("emissions"). Not every ion will produce emissions in all host materials, however. There are many examples in which radiation that has the potential for emission is quenched, or the energy transfer from the absorbing ions or the host material to the emitting ions is so poor that the radiation effects are barely observable. In other host materials, the radiation effects can be very large and with quantum efficiency near unity.

For a specific phosphor compound that does produce observable emissions, the spectral position(s) of the higher spectral energy content (or luminescent output) in its emissions (i.e., its "spectral signature") may be used to uniquely identify the phosphor compound from other compounds. Primarily, the spectral signature is due to the rare earth ion(s). However, spectral perturbations may be present due to the influence of the host material on the various emitting ions, typically through crystal field strength and splitting. This holds true for the temporal behavior of the emissions, as well.

The unique spectral properties of some phosphor compounds make them well suited for use in authenticating or identifying articles of particular value or importance (e.g., banknotes, passports, biological samples, and so on). Accordingly, luminescent phosphor compounds with known spectral signatures have been incorporated on or within various types of articles to enhance the ability to detect forgeries or counterfeit copies of such articles, or to identify and track the articles. For example, luminescent phosphor compounds have been incorporated on or within various types of articles in the form of additives, coatings, and printed or otherwise applied features that may be analyzed in the process of authenticating or tracking an article.

An article that includes a luminescent phosphor compound may be authenticated using specially designed authentication equipment. More particularly, a manufacturer may incorporate a known phosphor compound (e.g., an "authenticating" phosphor compound) into its "authentic" articles. Authentication equipment configured to detect the authenticity of such articles would have knowledge (e.g., stored information and/or a variety of spectral filters) of the wavelengths of absorbable excitation energy and the spectral properties of emissions associated with the authenticating phosphor compound. When provided with a sample article for authentication, the authentication equipment exposes the article to excitation energy having wavelengths that correspond with the known wavelengths of absorption features of the luminescent phosphor compound that lead directly or indirectly to the desired emissions. The authentication equipment senses and characterizes the spectral parameters for any emissions that may be produced by the article. When the spectral signal of detected emissions is within the authenticating parameter range of the detection apparatus that corresponds with the authenticating phosphor compound (referred to as the "detection parameter space"), the article may be considered authentic. Conversely, when the authentication equipment fails to sense signals expected within the detection parameter space, the article may be considered unauthentic (e.g., a forged or counterfeited article).

The above-described techniques are highly effective at detecting and thwarting relatively unsophisticated forgery and counterfeiting activities. However, individuals with the appropriate resources and equipment may be able to employ spectrometry techniques in order to determine the components of some phosphor compounds. The phosphor compounds may then be reproduced and used with unauthentic articles, thus compromising the authentication benefits that may otherwise be provided by a particular phosphor compound. Accordingly, although a number of phosphor compounds have been developed to facilitate article authentication in the above-described manner, it is desirable to develop additional compounds, unique ways of using such compounds with articles, and techniques for authenticating articles, which may render forgery and counterfeiting activities more difficult, and/or which may prove beneficial for identifying and tracking articles of particular interest. Furthermore, other desirable features and characteristics of the present invention will become apparent from the subsequent detailed description of the invention and the appended claims, taken in conjunction with the accompanying drawings and this background of the invention.

BRIEF SUMMARY

Embodiments of a method for identifying a luminescent material incorporated on or within an article include selectively exposing the article to excitation energy in an absorption band of the luminescent material, detecting first emission characteristics of first emitted radiation from the article within an emission band of the luminescent material when the article has a first temperature, and detecting second emission characteristics of second emitted radiation from the article within the emission band when the article has a second temperature that is different from the first temperature. Embodiments of the method further include determining whether the first emission characteristics are sufficiently different from the second emission characteristics.

Embodiments of an apparatus include a temperature adjustment element, an excitation energy generator, an emitted radiation detector, and a processing system. The temperature adjustment element is configured to adjust a temperature of an article proximate to the temperature adjustment element. The excitation energy generator is configured to provide excitation energy to the article, where the excitation energy corresponds to an absorption band of a luminescent material that is expected to be present when the article is authentic. The emitted radiation detector is configured to detect first emission characteristics of first emitted radiation within an emission band of the luminescent material when the article has a first temperature, and to detect second emission characteristics of second emitted radiation within the emission band when the article has a second temperature that is different from the first temperature. The processing system is configured to determine whether the first emission characteristics are sufficiently different from the second emission characteristics.

Embodiments of an article include a security feature that includes a medium and particles of a thermographic phosphor dispersed in the medium. The thermographic phosphor includes a host crystal lattice into which atoms of at least one emitting ion have been substituted. In an embodiment, the host crystal lattice is yttrium iron garnet (YIG) having the chemical composition $Y_3Fe_5O_{12}$, where Y is yttrium, Fe is iron, and O is oxygen, and the at least one emitting ion includes erbium ions substituted into the host crystal lattice at a substitution percentage.

BRIEF DESCRIPTION OF THE DRAWINGS

Embodiments of the present invention will hereinafter be described in conjunction with the following figures, wherein like numerals denote like elements, and wherein.

DETAILED DESCRIPTION

The following detailed description of various embodiments of the invention is merely exemplary in nature and is not intended to limit the inventive subject matter or the application and uses of the inventive subject matter. Furthermore, there is no intention to be bound by any theory presented in the preceding background or the following detailed description.

Embodiments discussed in detail below include articles that include thermographic phosphors, methods for producing such articles, and methods for detecting and identifying thermographic phosphors in the context of article authentication. The methods and apparatus for authenticating articles that include thermographic phosphors described below increase the diversity of available materials that may be used for authentication. The spectral signatures and decay time constants characterizing emissions from the thermographic phosphor embodiments discussed herein may be used as measurable quantities for the purpose of authentication.

As used herein, the term "thermographic phosphor" means a luminescent material having a significantly thermally dependent emission intensity and/or a significantly thermally dependent decay time constant. "Significantly thermally dependent," as it relates to an emission intensity and/or a decay time constant of a luminescent material, means that the luminescent material exhibits a detectable difference in emission intensity and/or decay time constant with respect to temperature of the thermographic phosphor (e.g., where the change is detectable by authentication apparatus such as the authentication apparatus described herein in conjunction with FIG. 3).

Figure 1:
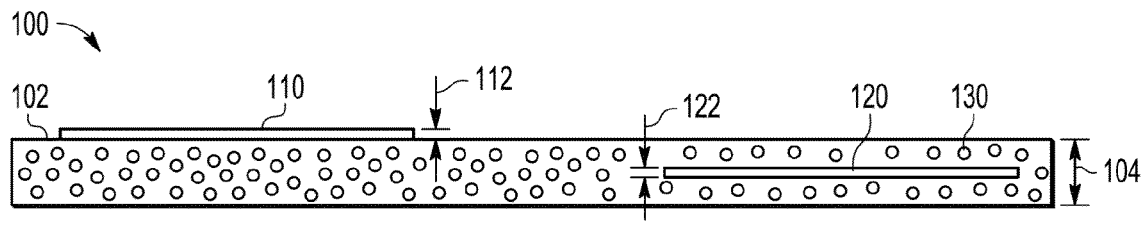
FIG. 1 is a cross-sectional, side view of an article that includes a substrate and an authentication feature that includes a thermographic phosphor, according to an example embodiment.

FIG. 1 depicts a cross-sectional view of an article 100 that includes a substrate 102 and one or more thermographic phosphors, according to an example embodiment. For example, an embodiment of an article 100 may include surface-applied and/or embedded authentication features 110, 120 that include thermographic phosphor particles (not shown in authentication features 110, 120), and/or the article 100 may include thermographic phosphor particles 130 that are evenly or unevenly dispersed within one or more components of the article 100 (e.g., within substrate 102 and/or one or more layers or other components of the article). Although article 100 is illustrated to include both surface-applied and/or embedded authentication features 110, 120 and particles 130, another article may include one or a combination of embedded authentication features, surface-applied authentication features, substrate-dispersed thermographic phosphor particles, and/or thermographic phosphor particles dispersed within one or more layers (not illustrated) of the article 100. Finally, although only one surface-applied authentication feature 110 and one embedded authentication feature 120 are shown in FIG. 1, an article may include more than one of either type of authentication feature 110, 120. The various relative dimensions of the authentication features 110, 120 and particles 130 are not to scale in FIG. 1.

In various embodiments, article 100 may be any type of article selected from a group that includes, but is not limited to, an identification card, a driver's license, a passport, identity papers, a value document (e.g., a banknote, a check, a document, a paper, a stock certificate, and so on), a packaging component, a credit card, a bank card, a label, a seal, a token (e.g., for use in gambling and/or with a gaming or vending machine), a postage stamp, a liquid, a human, an animal, and a biological sample. Substrate 102 may be any of various types of substrates, and includes one or more materials selected from a group that includes, but is not limited to, paper, a polymer, glass, a metal, a textile, and a fiber. Although inanimate, solid articles are discussed herein, it is to be understood that an "article" may include virtually any other object or material into or onto which a thermographic phosphor of an embodiment may be included.

Substrate 102, which may be rigid or flexible, may be formed from one or more layers or components, in various embodiments. The variety of configurations of substrate 102 are too numerous to describe herein, as the thermographic phosphors of the various embodiments may be used in conjunction with a vast array of different types of articles. Therefore, although a simple, unitary substrate 102 is illustrated in FIG. 1, it is to be understood that substrate 102 may have any of a variety of different configurations. For example, a substrate may be a "composite" substrate that includes a plurality of layers or sections of the same or different materials. For example, but not by way of limitation, a substrate may include one or more paper layers or sections and one or more plastic layers or sections that are laminated or otherwise coupled together to form the composite substrate (e.g., a paper layer/plastic layer/paper layer or plastic layer/paper layer/plastic layer composite substrate).

Surface-applied authentication feature 110 may be, for example but not by way of limitation, a printed authentication feature or an authentication feature that includes one or more rigid or flexible materials into which or onto which a thermographic phosphor of an embodiment is included. For example, but not by way of limitation, the surface-applied authentication feature 110 may comprise an ink, pigment, coating, or paint that includes particles of a thermographic phosphor of an embodiment. Alternatively, the surface-applied authentication feature 110 may comprise one or more rigid or flexible materials into which or onto which particles of a thermographic phosphor of an embodiment are included, where the substrate is then adhered or otherwise attached to a surface of the article substrate 102. According to various embodiments, surface-applied authentication feature 110 may have a thickness 112 of about one micron or more, and surface-applied authentication feature 110 may have a width and length that is less than or equal to the width and length of the substrate 102.

Embedded authentication feature 120 comprises one or more rigid or flexible materials in which or onto which a thermographic phosphor of an embodiment is included. For example, but not by way of limitation, embedded authentication feature 120 may be configured in the form of a discrete, rigid or flexible substrate, a security thread, or another type of structure. According to various embodiments, embedded authentication feature 120 may have a thickness 122 in a range of about one micron up to the thickness 104 of the substrate 102, and embedded authentication feature 120 may have a width and length that is less than or equal to the width and length of the substrate 102.

As mentioned above, thermographic phosphor particles 130 may be evenly or unevenly dispersed within substrate 102 (or a portion of substrate 102), as shown in FIG. 1, or within one or more other components of the article 100 (e.g., within one or more layers or other components of the article), in other embodiments. The thermographic phosphor particles 130 may be dispersed within substrate 102 or another component, for example but not by way of limitation, by mixing particles 130 into a base material for the substrate 102 or other component, and/or by impregnating the substrate 102 or other component with a colloidal dispersion of the particles 130, as discussed previously.

According to an embodiment, the thermographic phosphor from which thermographic phosphor particles 130 are formed includes a host crystal lattice and one or more emitting ions substituted into crystallographic sites of the host crystal lattice. The emitting ion(s) are capable of producing detectable radiation upon receiving excitation energy within absorption band(s) of the emitting ion(s). The emitting ion(s) may receive energy for subsequent radiation through one or more of multiple mechanisms. For example, an emitting ion may be capable of directly absorbing excitation energy within an absorption band of the emitting ion, and the emitting ion may thereafter radiate at least some of the absorbed energy (typically at a different and longer wavelength from the excitation energy). Alternatively, as is described below, an emitting ion may be capable of indirectly absorbing excitation energy from the host crystal lattice and/or from one or more other ions substituted into crystallographic sites of the host crystal lattice.

For example, in some embodiments, the host crystal lattice may absorb excitation energy and transfer some of that energy to the emitting ion(s) (and/or to one or more sensitizing or cascade ion(s)). In addition, in various embodiments, the thermographic phosphor also may include one or more sensitizing ions and/or cascade ions substituted into crystallographic sites of the host crystal lattice. Each sensitizing ion, when included, may absorb excitation energy within an absorption band of the sensitizing ion, and may transfer at least some of that energy to the emitting ion(s) and/or to the cascade ion(s). Each cascade ion, when included, may absorb excitation energy from the sensitizing ion(s), and may transfer at least some of that energy to the emitting ion(s). An "absorbing ion" refers to an ion of a thermographic phosphor that is capable of absorbing appropriate excitation energy and thereafter radiating some of the absorbed energy and/or transferring it to another ion (e.g., ultimately to an emitting ion). In various embodiments, an emitting ion, a sensitizing ion, and/or a cascade ion may be considered to be an absorbing ion. As used herein, "appropriate excitation energy" refers to excitation energy having a range of wavelengths that corresponds to an absorption band of an absorbing ion of thermographic phosphor.

As indicated above, the host crystal lattice comprises a material into which the emitting ion(s) (and the sensitizing and cascade ion(s), if included) are incorporated (i.e., substituted for one or more substitutable elements of the host crystal lattice). More particularly, the host crystal lattice is a crystal lattice into which different chemical constituents may substitute at various crystallographic positions or sites within the lattice. The term "substitutable element," as used herein, refers to an element of the host crystal lattice that occupies certain sites within the crystal structure, where another element (e.g., emitting, sensitizing, and/or cascade ions) may be substituted into those sites during formation of the thermographic phosphor. Each atom of the host crystal lattice that allows for replacement with an emitting, sensitizing or cascade ion has a similar size, similar loading, and similar coordination preference as the ion it will be replaced with. During formation of the thermographic phosphor, the atoms in each position within the host crystal lattice will be accounted for by atomic percent.

According to an embodiment, the host crystal lattice is yttrium iron garnet (YIG) into which erbium (Er) ions have been substituted. This combination is referred to herein as Er:YIG. YIG has the chemical composition $Y_3Fe_5O_{12}$, where Y is yttrium, Fe is iron, and O is oxygen. Yttrium functions as a substitutable element, and erbium is substituted into some of the yttrium sites at a certain substitution percentage (described herein in terms of atomic percent). According to an embodiment, the thermographic phosphor includes YIG with erbium substituted at a substitution percentage in a range of about 0.5 atomic percent to about 50 atomic percent, although the erbium may be substituted at substitution percentages greater than or less than this range, as well. Essentially, the erbium may be substituted at any percentage that is high enough to produce detectable emissions and that is low enough to avoid complete concentration quenching of the emissions.

Although the description, below, primarily uses YIG as an example of a host crystal lattice and erbium as an example of an emitting ion suitable for use with the various thermographic phosphor embodiments, it is to be understood that host crystal lattices other than YIG and/or emitting ions other than erbium also could be used, and such alternate embodiments are considered to be within the scope of the inventive subject matter. For example, a YIG/YAG host crystal lattice (e.g., with the YAG component being less than about 30 percent of the material) with substituted erbium may be a suitable thermographic phosphor, along with various other host crystal lattices and/or emitting ions. More particularly, any thermographic phosphor that exhibits a detectable change in emission intensity and/or decay time constant with respect to temperature may be suitable for use with the various embodiments.

When appropriate excitation energy is directed toward a thermographic phosphor of an embodiment, the excitation energy is absorbed by one or more "absorbers" within the thermographic phosphor, and emitting ions within the thermographic phosphor may produce detectable emissions. The emitting ions may be an absorber, and/or atoms other than the emitting ions may function as an absorber. For example, in embodiments in which the thermographic phosphor is Er:YIG, the iron may function as a primary absorber of appropriate excitation energy (e.g., excitation energy in an iron absorption band), and the iron may transfer some of the absorbed energy to the erbium. In addition, the erbium may function as an absorbing ion, which may directly absorb appropriate excitation energy (e.g., excitation energy in an erbium absorption band). Either way, the erbium may thereafter emit detectable radiation within one or more erbium emission bands. As will be discussed in more detail later, erbium produces relatively strong emissions at wavelengths in a range of about 1460 nanometers (nm) to about 1660 nm, with multiple emission peaks being present within this range. As used herein, an "emission band" means a continuous range of wavelengths of the electromagnetic spectrum within which concentrated, non-negligible (e.g., detectable) emissions occur from one or more emitting ions of the thermographic phosphor. For any particular emitting ion, an "emission band" is bounded by a lower wavelength below which emissions are negligible for that ion, and an upper wavelength above which emissions are negligible for that ion.

Figure 2:
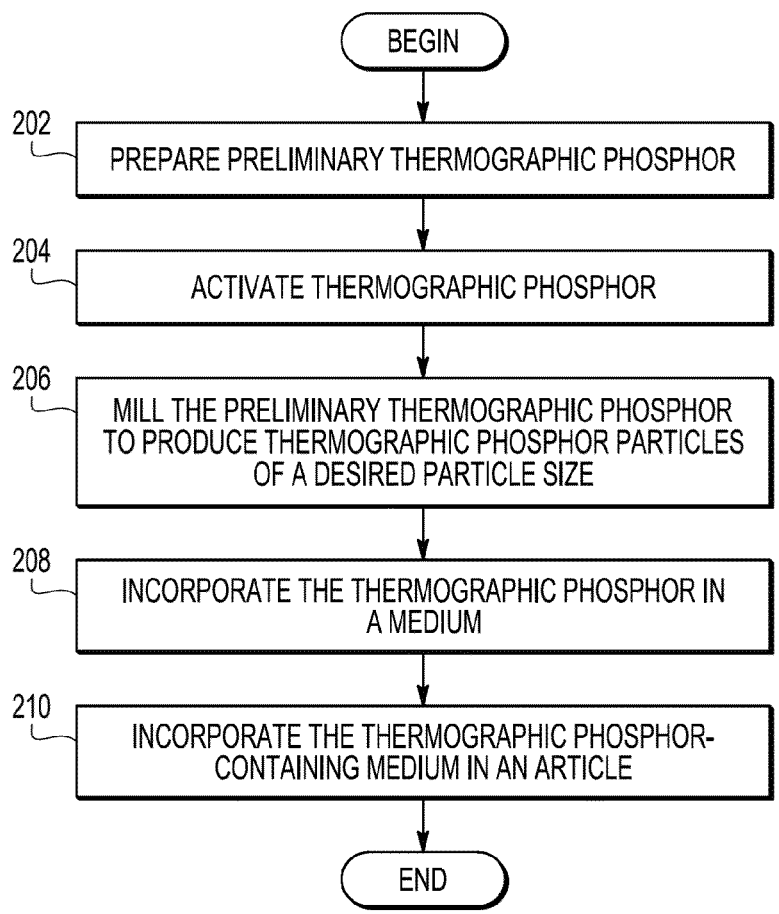
FIG. 2 is a flowchart of a method for producing an article that includes a thermographic phosphor, in accordance with an example embodiment.

FIG. 2 is a flowchart of a method for producing a thermographic phosphor (e.g., a thermographic phosphor used in article 100, FIG. 1), a medium that includes the thermographic phosphor, and an article (e.g., article 100, FIG. 1) that includes the thermographic phosphor-containing medium, in accordance with an example embodiment. The method begins, in block 202, by preparing a preliminary thermographic phosphor which, according to an embodiment, includes Er:YIG. Generally, a luminescent material (e.g., a thermographic phosphor) may be created using any of a number of conventional processes that are known to those of skill in the art. For example, formation of preliminary thermographic phosphors of the various embodiments may be achieved using solid state chemistry, as described below. More specifically, according to an embodiment, the preliminary thermographic phosphor is prepared by growing a crystal using components that include all of the elements of the thermographic phosphor, typically in the form of oxides.

For example, a thermographic phosphor having the formula $Y_3Fe_5O_{12}$, may be prepared using solid state chemistry. More particularly, to incorporate yttrium and iron in the preliminary thermographic phosphor, yttrium oxide ($Y_2O_3$) and iron oxide ($Fe_2O_3$) are two of the components used to grow the preliminary thermographic phosphor. In addition, atom-for-atom replacements of the yttrium in the crystal lattice may be achieved by including erbium oxide ($Er_2O_3$) as an additional component used to grow the preliminary thermographic phosphor. In order to substitute erbium into the yttrium sites of the preliminary thermographic phosphor, some or all of the yttrium oxide is replaced with desired amounts of erbium oxide, where replacement quantities are defined in terms of atomic number (i.e., indicating the percentage of yttrium atoms replaced with erbium atoms). For example, if it were desired to have 12 percent substitution of erbium in the yttrium sites of the preliminary thermographic phosphor, 12 percent of the yttrium oxide would be replaced with erbium oxide.

Once combined in the appropriate quantities (e.g., in quartz boats and/or alumina crucibles), the thermographic phosphor is activated, in block 204, by firing the combined components one or more times at one or more prescribed temperatures (e.g., temperatures in a range of about 500-1200 degrees Celsius, or a different range) for one or more prescribed times (e.g., one or more hours). Powderizing processes may be performed after some or all of the firing steps, in some embodiments. In addition, in embodiments in which a fluxing agent is used, the fluxing agent may be washed out of the preliminary thermographic phosphor after the final firing step. The resulting, powderized crystal thus forms the preliminary thermographic phosphor. Ultimately, according to an embodiment, the erbium has a +3 valence state.

Although solid state chemistry may be used to create the preliminary thermographic phosphor, as discussed above, in other cases, solution chemistry techniques may be used. Using solution chemistry, the various materials are dissolved, precipitated, and fired. Depending on the particular process used to create the thermographic phosphor, other materials may be included in forming the preliminary thermographic phosphor. For example, various fluxing agents and other precursors may be included within the preliminary thermographic phosphor.

In block 206, the preliminary thermographic phosphor may be further milled and/or filtered to produce crystal particles of desired sizes from particles that were produced from the run that were larger. For example, it has been found that the efficiency of the various embodiments of thermographic phosphors described herein may remain relatively high even when the thermographic phosphor powder includes particles with particle sizes of less than about 10 microns, and in some cases particles having sizes as low as about 1 micron or less. As used herein, the term "particle size" is defined as a particle mean diameter (e.g., a mass volume 50 percent point (D50) particle size mean diameter, as measured by a laser light diffraction type of measurement device, such as a device produced by Microtrac Inc. of Montgomeryville, Pa.).

In block 208, the thermographic phosphor particles are incorporated into a medium. For example, but not by way of limitation, the medium may correspond to a substrate of an article (e.g., a plastic, plastic base resin, a glass, a ceramic, a metal, a textile, wood, fiber, paper pulp, paper, and mixtures thereof), or the medium may correspond to a material that may be applied to (e.g., printed on, coated on, sprayed on, or otherwise adhered to or bonded to) the surface of an article substrate (e.g., an ink, an ink additive, a glue, a liquid, a gel, a plastic, and a plastic base resin), or a feature that is embedded within a substrate (e.g., an embedded feature, a security thread, and so on). In the former case, the thermographic phosphor particles may be incorporated into a substrate material, for example, by combining the thermographic phosphor particles with a base material (e.g., paper, paper pulp, a polymer, plastic, plastic base resin, glass, metal, a textile, fiber, ceramic, wood, a slurry, mixtures thereof, and so on) for the substrate, and/or by impregnating the substrate with a colloidal dispersion of the thermographic phosphor particles. Impregnation may be performed, for example, by a printing, dripping, coating or spraying process.

In embodiments in which the thermographic phosphor particles are incorporated into a material that may be applied on a surface of a substrate, the thermographic phosphor particles are mixed in with a composition (e.g., an ink, ink additive or other carrier). In embodiments in which the thermographic phosphor particles are incorporated into a feature that is embedded within a substrate, incorporation of the thermographic phosphor particles into the feature may be performed in a similar manner to incorporation of the thermographic phosphor into the substrate, as discussed above. More particularly, the thermographic phosphor particles may be mixed with a base material from which the embedded feature is formed. In still other embodiments, thermographic phosphor particles may be incorporated or combined with other media (e.g., glues, various liquids, gels, and so on).

In block 210, an article is produced that includes the thermographic phosphor. For example, this may be accomplished by incorporating the thermographic phosphor-containing medium or feature in or on an article (e.g., article 100, FIG. 1). In embodiments in which the thermographic phosphor-containing medium is the base material for the substrate, this step may be bypassed. Conversely, in embodiments in which the thermographic phosphor-containing material is applicable to a surface of the substrate, the thermographic phosphor-containing material may be printed onto one or more surfaces of the substrate in pre-determined locations. Conversely, when the thermographic phosphor-containing material corresponds to an embedded feature, the embedded feature is integrated with the substrate material when the substrate material is in a malleable form (e.g., when the material is a slurry, molten, or non-cured form). In any one of the above-described manners, an embodiment of a thermographic phosphor may be incorporated within an article.

Embodiments of thermographic phosphors described herein are particularly well suited for use in conjunction with security or authentication features of an article (e.g., features of an article that may be analyzed to determine authenticity of the article), although they may be used for other purposes, as well. More particularly, the absorption and emission properties of embodiments of thermographic phosphors discussed herein are suitable for the use of the thermographic phosphors in conjunction with security and authentication features.

For example, using authentication equipment such as that described below in conjunction with FIG. 3, an article may be presented to the authentication equipment, and a portion of the article on or within which a thermographic phosphor is incorporated optionally may be heated or cooled to a first temperature. Alternatively, the portion of the article may remain at an ambient first temperature, which may be sensed by the authentication equipment.

To produce a first result, the portion of the article may then be exposed to appropriate excitation energy. For example, in embodiments in which an Er:YIG thermographic phosphor is incorporated on or within an article, the thermographic phosphor in the exposed portion of the article may be excited with excitation energies in the iron and/or erbium absorption bands. In such embodiments, the erbium may produce detectable emissions in one or more erbium emission bands (e.g., emission band ranging from about 1460 nm to about 1660 nm). Upon discontinuation of the provision of the excitation energy, the authentication equipment detects the emission intensity and/or decay time constant of the erbium emissions (in all or part of that spectral range) at the first temperature, and stores this first result.

According to an embodiment, to produce a second result, the authentication equipment then heats or cools the portion of the article to a second temperature (or passively allows the portion of the article to adjust to the second temperature by discontinuing active heating or cooling of the portion of the article). The portion of the article may again be exposed to appropriate excitation energy. Upon discontinuation of the provision of the excitation energy, the authentication equipment again detects the emission intensity and/or decay time constant of the erbium emissions (in the same spectral range as the detection that produced the first result) at the second temperature, and stores the result. According to an embodiment, the authentication equipment then determines whether the changes in the emission intensity and/or the change in the decay time constant associated with the first and second results are significant enough to fall within a detection parameter space.

Figure 3:
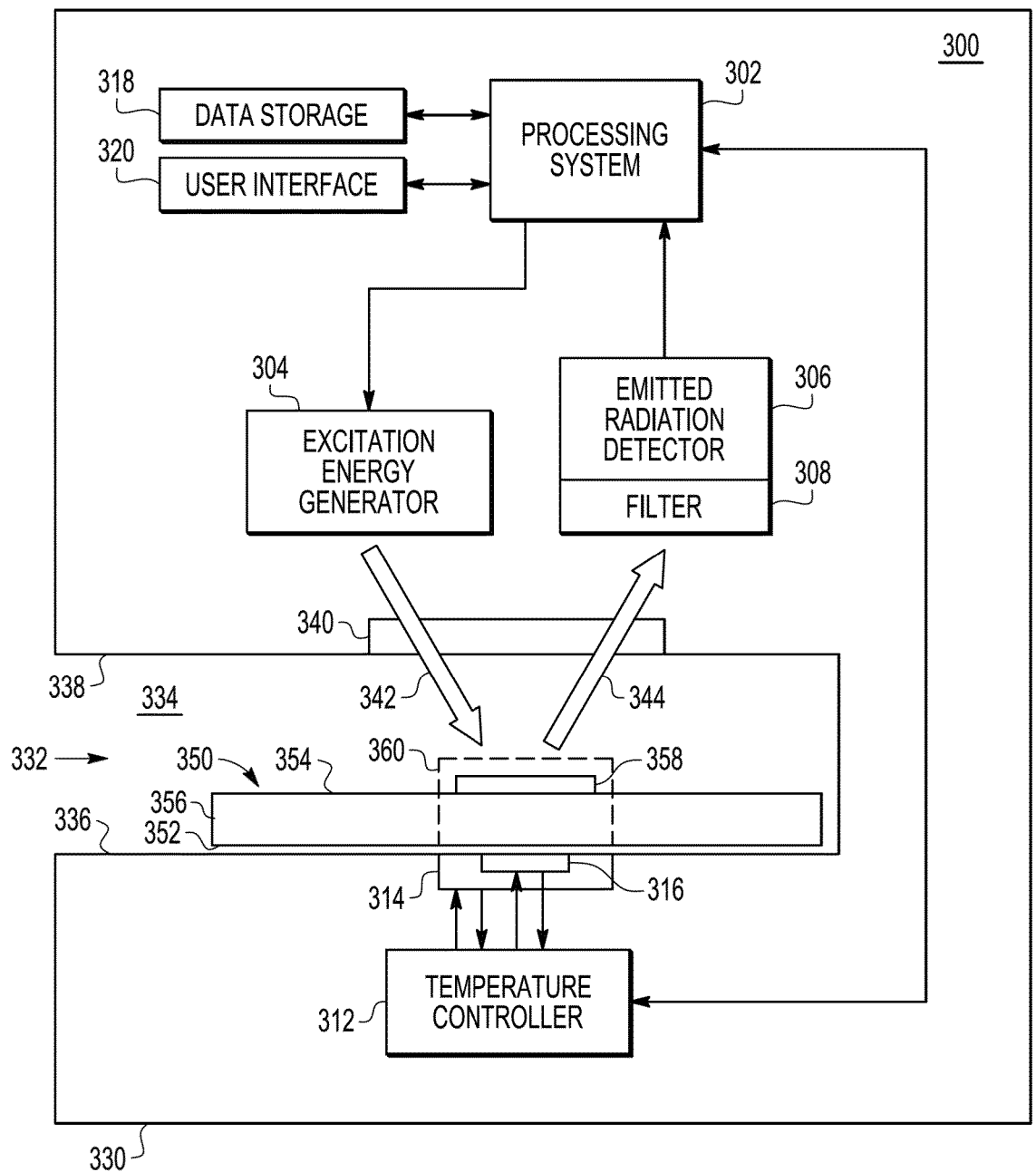
FIG. 3 is a simplified diagram of a system for authenticating an article, in accordance with an example embodiment.

FIG. 3 is a system 300 for authenticating an article 350, in accordance with an example embodiment. System 300 includes a processing system 302, at least one excitation energy generator 304, at least one emitted radiation detector (or photodetector) 306 with associated optical filter 308, a temperature controller 312, at least one temperature adjustment element 314, at least one temperature sensor 316, data storage 318, and a user interface 320, according to an embodiment. It is to be understood that the various components of system 300 may not be drawn to scale in FIG. 3.

In conjunction with authenticating an article (e.g., article 350), and as will be described in more detail below, processing system 302 may control the provision of excitation energy 342 by excitation energy generator 304, the analysis of emitted radiation 344 detected by emitted radiation detector 306, and the timing of temperature adjustments and sensing operations that are coordinated by temperature controller 312, according to an embodiment. Processing system 302 may include one or more processors and associated circuitry, which are configured to implement such control and analysis processes (e.g., in the form of executable software algorithms) according to various embodiments, and as will be described below in more detail. Similarly, temperature controller 312 may include one or more processors and associated circuitry, which are configured to implement control and analysis processes (e.g., in the form of executable software algorithms) specifically associated with controlling temperature adjustments and sensing operations performed by temperature adjustment element 314 and temperature sensor 316, respectively, based on inputs from processing system 302. According to an embodiment, processing system 302 communicates control commands (e.g., timing commands, temperature settings, and so on) to temperature controller 312, and temperature controller 312 communicates operational data (e.g., sensed temperatures, and so on) to processing system 302. In an alternate embodiment, processing system 302 and temperature controller 312 may be implemented using common hardware. For purposes of clarity, however, they are depicted as separate elements.

System 300 is configured to authenticate an article (e.g., article 350) by directing excitation energy toward the article 350, detecting emissions (if any) from the article 350 at multiple temperatures, and analyzing the differences (if any) between characteristics of the emissions at the multiple temperatures. Although various embodiments of systems (e.g., system 300) may be configured to authenticate any of a variety of differently-shaped and configured substantially two-dimensional and/or three-dimensional articles (including embodiments of articles described in conjunction with FIG. 1), an example is provided herein of a system 300 configured to authenticate a substantially two-dimensional article (e.g., article 350, FIG. 3).

In the example, article 350 includes a substrate 356 and, optionally, a surface-applied or embedded authentication feature 358. Either the substrate 356, the surface-applied or embedded authentication feature 358, a layer or other component of article 350, or any combination thereof may include a thermographic phosphor, as described above in conjunction with FIG. 1. For purposes of explaining an embodiment of authentication system 300, the description below uses an example in which surface-applied authentication feature 358 includes a thermographic phosphor. It is to be understood that the example provided should not be construed as a limitation. In addition, although the example method and article embodiments described herein discuss articles that include a single thermographic phosphor that is detected using a single iteration of a method described in conjunction with FIG. 4, it is to be understood that an article may include multiple different thermographic phosphors (e.g., each having different emissions characteristics) that are detected using multiple iterations of the method described in conjunction with FIG. 4.

In addition to the components previously described, system 300 also may include a housing 330 to provide structural support for the various components of system 300, and within which some or all of the various components of system 300 may be substantially enclosed. Although a housing 330 having a certain configuration is illustrated in FIG. 3 and described herein, it is to be understood that the housing 330 could be significantly differently configured, in other embodiments, while still providing the desired functionality of the housing 330. For example, instead of a unitary housing 330, as shown, other embodiments may include a structure having multiple parts (e.g., upper and lower housing portions) that are hinged or otherwise configurable to provide a desired juxtaposition of system components with respect to an article (e.g., a juxtaposition of temperature adjustment element 314 and window 340 with respect to article 350).

According to an embodiment, housing 330 includes an opening 332 to an interior chamber 334. The opening 332 and chamber 334 are configured to accommodate an article (e.g., article 350) that is presented for authentication (e.g., manually or automatically). For example, the chamber 334 may be defined, at least in part, by a chamber lower surface 336 and a chamber upper surface 338. The chamber lower surface 336 may be configured so that at least a portion of a bottom surface 352 of the article 350 is proximate to a portion of the chamber lower surface 336 at which the temperature adjustment element 314 and the temperature sensor 316 are located. The temperature adjustment element 314 may be oriented so that the temperature adjustment element 314 directly contacts the bottom surface 352 of the article 350, thus providing good thermal transfer between the temperature adjustment element 314 and the article 350.

Under control of the temperature controller 312, the temperature adjustment element 314 is configured to heat and/or cool a portion (e.g., portion 360) of the article 350 to a target temperature that is known to the temperature controller 312. As will be described in more detail later, the target temperature may be specified by the processing system 302 to the temperature controller 312 based on temperature settings stored in data storage 318 and/or based on temperature settings specified by a user of the system 300 via user interface 320. In addition, processing system 302 may provide control signals to temperature controller 312 that affect the timing (e.g., start time, stop time, and/or duration) of temperature adjustments made by temperature adjustment element 314.

According to various embodiments, temperature adjustment element 314 may include a distinct heating element and/or a distinct cooling element. For example, temperature adjustment element 314 may include a resistive type of heater, which includes at least one resistive element coupled with at least one capacitor, in an embodiment. During operation, the capacitor(s) are charged with an amount of energy that corresponds to a desired temperature increase for the article 350, and when the energy stored in the capacitor(s) is released through the resistive element(s), the heat generated in the resistive element(s) may transfer to the article 350. In an alternate embodiment, rather than dumping energy stored in a capacitor through a resistive element, the system may apply current through the resistive element(s) for a pre-determined amount of time (for a given supply voltage), in order to provide a quantity of energy that corresponds to the desired temperature increase for the article 350.

Alternatively, temperature adjustment element 314 may include a heat pump. For example, temperature adjustment element 314 may include a thermoelectric heater/cooler (TEC), which transfers heat from one side of the device to the other side, where the direction of heat transfer depends on the polarity of the electrical current flow applied to the TEC. Accordingly, a TEC is capable of both heating and cooling a portion (e.g., portion 360) of an article (e.g., article 350). More particularly, current flow in a first direction through the TEC may cause the article-facing side of the TEC to heat up to a temperature that is greater than the temperature of the portion of the article. This causes heat to be transferred from the TEC to the portion of the article, which may result in an increase the temperature of the portion of the article (i.e., heating of the portion of the article). Conversely, current flow in the opposite direction through the TEC may cause the article-facing side of the TEC to cool down to a temperature that is less than the temperature of the portion of the article. This causes heat to be transferred from the portion of the article to the TEC, which may result in a decrease in the temperature of the portion of the article (i.e., cooling of the portion of the article).

According to an embodiment, temperature sensor 316 is configured to sense the temperature of the portion of the article. The temperature sensor 316 may provide the sensed temperature measurements to temperature controller 312 as a feedback signal, and the temperature controller 312 may analyze the sensed temperature measurements to determine, for example, whether the temperature of the portion of the article has reached a target temperature. Temperature controller 312 may provide signals to processing system 302 that indicate that the portion 360 of the article 350 has reached the target temperature, and/or temperature controller 312 may provide signals to processing system 302 that indicate the sensed temperature of the portion 360 of the article 350 at various times. The temperature adjustment element 314 and the temperature sensor 316 may be integral with each other or they may be positioned in contact with each other (e.g., side by side with both the temperature adjustment element 314 and the temperature sensor 316 being in thermal contact with the article 350). In an alternate embodiment, system 300 does not include a temperature sensor 316.

The chamber upper surface 338 may include one or more windows 340 through which excitation energy 342 may be provided by excitation energy generator 304 to a portion of an upper surface of the article (e.g., upper surface 354), and through which emitted radiation 344 emanating from the portion of the upper surface of the article may be received by emitted radiation detector 306 and its associated filter 308, as will be discussed in more detail below. According to an embodiment, the window 340 is located directly across the chamber 334 from the temperature adjustment element 314 and the temperature sensor 316, so that the excitation energy 342 may be provided to a same portion of the article (e.g., portion 360) that is heated and/or cooled by temperature adjustment element 314, and so that any emitted radiation 344 from the article 350 emanates from the same portion of the article (e.g., portion 360) that is heated and/or cooled by temperature adjustment element 314. According to an embodiment, the window 340 and the temperature adjustment element 314 are oriented, with respect to the chamber upper surface 338 and the chamber lower surface 336, respectively, so that a relatively small air gap (not illustrated) is maintained between the window 340 and the top surface 354 of the article 350 for the purpose of providing insulation.

In alternate embodiments, either or both the temperature adjustment element 314 and/or the temperature sensor 316 may be positioned on the same side of chamber 334 as the window 340 (e.g., on chamber upper surface 338), as long at the temperature adjustment element 314 and/or temperature sensor 316 are positioned so that they may heat and/or cool a same portion 360 of the article 350 from which emitted radiation 344 emanates (and to sense the temperature of that portion 360 of the article 350), and so that the temperature adjustment element 314 and/or temperature sensor 316 do not block or interfere with emitted radiation 344 traveling through window 340.

According to an embodiment, processing system 302 also is configured to provide control signals to excitation energy generator 304, which cause excitation energy generator 304 to direct excitation energy 342 toward article 350 through window 340. More specifically, processing system 302 provides control signals to the excitation energy generator 304 to direct excitation energy 342 toward article 350 for a sufficient period of time to excite emitting ions in an authentic thermographic phosphor, if any, which is incorporated in the portion 360 of the article 350 under window 340 (e.g., emitting ions in substrate 356 and/or authentication feature 358). Processing system 302 then controls the excitation energy generator 304 to discontinue provision of the excitation energy 342, and emitted radiation 344 from the portion 360 of the article 350 that travels through window 340 is detected using filter 308 and emissions detector 306.

In the control signals to the excitation energy generator 304, processing system 302 may specify the timing (e.g., start time, stop time, and/or duration) of the provision of excitation energy 342, and/or other parameters associated with the particular excitation energy 342 to be generated (e.g., intensities and/or other parameters). Typically, the bandwidth of the excitation energy 342 is pre-determined based on the excitation source that is included as part of the excitation energy generator 304 (e.g., the bandwidth of excitation energy produced by a selected light emitting diode or laser diode). As discussed previously, appropriate excitation energy for a thermographic phosphor of an embodiment may be in an iron and/or erbium absorption band, in various embodiments. The various timing and/or radiation generation parameters may be retrieved from data storage 318, for example. Excitation energy generator 304 may include, for example, one or more lasers, laser diodes, light-emitting diodes (LEDs), incandescent filaments, lamps, or other excitation sources.

In addition to controlling excitation energy generator 304, processing system 302 is configured to provide control inputs to emissions detector 306, which cause emissions detector 306 to attempt to detect emitted radiation 344 emanating from a portion 360 of the article 350 in response to emitting ions of a thermographic phosphor having absorbed (either directly or indirectly) at least some of the excitation energy 342. For example, the portion 360 of the article 350 may produce emissions corresponding to erbium emissions, in an embodiment. In other embodiments, the portion 360 of the article 350 may produce emissions corresponding to emissions from other emitting ions.

Emissions detector 306 may include, for example, a spectral filter 308, one or more electro-optical sensors, photomultiplier tubes, avalanche photodiodes, photodiodes, charge-coupled devices, charge-injection devices, photographic films, or other detection devices. In a particular embodiment, emissions detector 306 includes a spectral filter 308 positioned between window 340 and a photodetector. The spectral filter 308 is configured to filter the emitted radiation 344 before it is provided to detector 306, so that emissions only within an emission band (i.e., a subset of the entire spectrum) actually impinge upon the active area of detector 306. The spectral filter 308 may include, for example, a long pass, bandpass, or other type of filter configured to pass light only within a spectral band of interest, and to reject all other light.

Detector 306 has sensitivity within a spectral band of interest, and accordingly may detect light passing through the spectral filter 308 that is within that spectral band. According to an embodiment, detector 306 is configured to detect emissions within a channel corresponding to an erbium emission band. According to an embodiment, detector 306 includes an indium-gallium-arsenide (InGaAs) detector (e.g., a telecom type or extended InGaAs). Depending on the wavelengths of emissions that are desired to be detected, other types of detectors that are capable of detecting emissions within a band of interest may be used in other embodiments (e.g., silicon, lead-sulfide, lead-selenide, germanium, indium-antimonide, indium-arsenide, platinum-silicide, indium-antimonide, and so on).

Detector 306 produces electronic signals that are proportional to the intensity of the collected radiation that impinges on the active area of the detector 306. More particularly, detector 306 provides signals (e.g., one or more digitized intensity values) to processing system 302 representing integrated intensities of the portion of the emitted radiation 344 that is received by the detector 306. As used herein, the term "intensity" may mean an integrated intensity detected over a range of wavelengths, although the term "intensity" also could be interpreted as an intensity detected at a particular wavelength (e.g., a peak intensity).

According to an embodiment, upon discontinuation of excitation energy 342, emissions detector 306 digitizes one or more integrated intensity values. For example, the emissions detector 306 may produce a first value representing an integrated intensity detected at about t=0, and then may produce one or more additional values representing integrated intensities detected at one or more pre-selected intervals thereafter (e.g., at a time that corresponds to the decay time constant for an authentic thermographic phosphor, and/or at one or more additional times). The intensity values provided by emissions detector 306 to processing system 302 enable processing system 302 to determine one or more emission characteristics (e.g., one or more temporal and/or spectral characteristics of the emitted radiation 344). For example, in the context of authenticating an article 350, emissions detector 306 may produce one value corresponding to a single integrated intensity of emitted radiation in an erbium emission band, or may produce a series of values (e.g., two or more values) corresponding to multiple, temporally-spaced integrated intensities of emitted radiation in an erbium emission band. Each value or sets of values from detector 306 may be tagged or otherwise associated with information indicating a time when the emissions were detected (e.g., a time from discontinuation of provision of the corresponding excitation energy 342).

As mentioned above and as will be explained in more detail below, an embodiment of an authentication method includes attempting to cause an article (e.g., article 350) to produce detectable emissions at two or more different temperatures, and thereafter analyzing differences, if any, between characteristics of the emissions at the two or more different temperatures. In the embodiment described below and depicted in FIG. 4, the method includes attempting to cause the article to produce detectable emissions at first and second temperatures that are achieved through active control of a temperature adjustment element (e.g., temperature adjustment element 314). In another embodiment, either the first temperature or the second temperature may be an ambient temperature, and thus only one of the first or second temperatures is produced through active control of the temperature adjustment element. In still other embodiments, the method may include attempting to cause the article to produce detectable emissions at more than two temperatures and analyzing differences between characteristics of the emissions at the more than two temperatures. In such an embodiment, any one of the temperatures may be ambient temperature. This latter embodiment is not described in detail herein, although it is intended to be included in the scope of the described embodiments.

Various embodiments of methods for performing article authentication using an authentication system (e.g., system 300, FIG. 3) will now be described in conjunction with FIG. 4. Understanding of the authentication method embodiments will be facilitated by continued reference to FIG. 3. It is to be understood, however, that the authentication method embodiments may be carried out using systems that are configured differently from the authentication system embodiments described in conjunction with FIG. 3. Similarly, the authentication system embodiments described in conjunction with FIG. 3 may carry out authentication methods that are different from the authentication method embodiments described in conjunction with FIG. 4.

Figure 4:
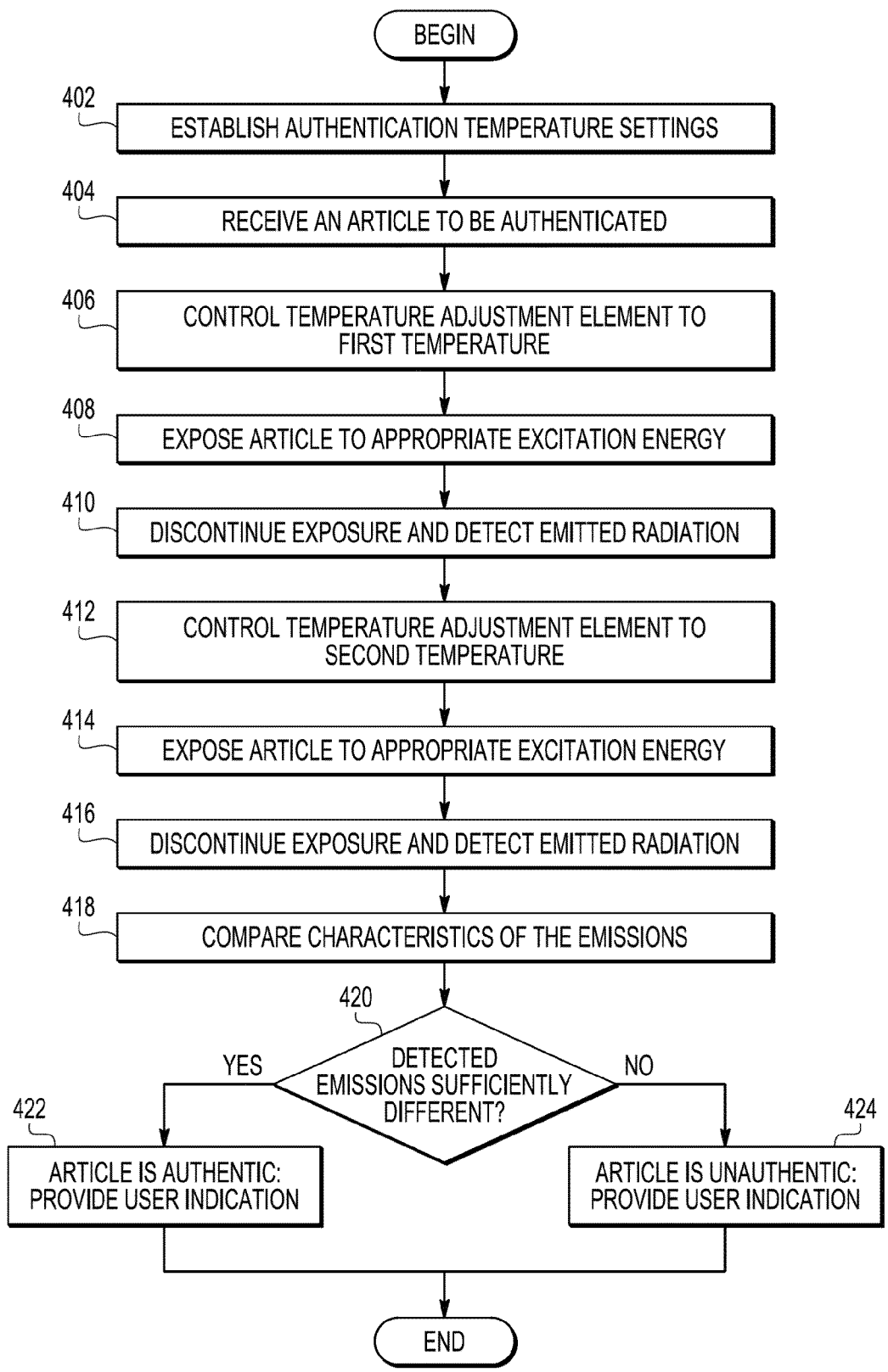
FIG. 4 is a flowchart of a method for performing authentication of an article, in accordance with an example embodiment.

Referring now to FIG. 4 and with continued reference to FIG. 3, a flowchart of a method for performing authentication of an article (e.g., article 100, 350, FIGS. 1, 3) is described in accordance with an example embodiment. The method may begin, in block 402, by establishing settings for one or more temperatures associated with the authentication process. As used herein, a "temperature" associated with the authentication process may be an actual temperature that is sensed (e.g., by temperature sensor 316). For example, the temperature may correspond to the sensed temperature of a portion (e.g., portion 360) of an article (e.g., article 350) that is in contact with a temperature sensor (e.g., temperature sensor 316). In an alternate embodiment, a "temperature" may be a temperature that is defined based on a setting, rather than an actual, sensed temperature. In the latter embodiment, the authentication system (e.g., system 300) may exclude a temperature sensor (e.g., temperature sensor 316). As used herein, the term "ambient temperature" means a steady-state temperature that is not a result of a temperature adjustment (e.g., by temperature adjustment element 314).

In block 402, the system may first be configured by establishing one or more settings for authentication temperatures to be used during the authentication process. According to an embodiment, the authentication temperature setting(s) may be established by a user of the system through manipulation of a user interface (e.g., user interface 320). The user interface may include one or more keys, dials, displays, and other user interface components, which enable the user to specify the temperature(s). Once specified, the temperature(s) are stored in data storage (e.g., data storage 318). In an embodiment, the temperature(s) may be specified in terms of absolute temperatures (e.g., a temperature value in degrees Celsius or Fahrenheit). In an alternate embodiment, the temperature(s) may be specified in terms of a temperature difference. For example, a temperature may be specified as a temperature difference from another pre-defined or user-specified temperature, or as a temperature difference from an ambient temperature (e.g., an ambient temperature that is sensed at a time when the authentication process is performed), in various embodiments.

According to an embodiment, whether specified by the user or pre-defined, the first temperature and the second temperature are different from each other by a temperature difference in a range of about +/−5 degrees Celsius to about +/−15 degrees Celsius. In a more specific embodiment, the first and second temperatures are different from each other by a temperature difference of about +/−10 degrees Celsius. For example, in an embodiment, the first temperature may be about 33 degrees Celsius, and the second temperature may be either about 23 degrees Celsius or about 43 degrees Celsius, although the first and second temperatures may be different, as well. In an embodiment in which the temperatures are user-specified, during execution of block 402, the system may restrict the user to selecting first and second temperatures that are different from each by a temperature difference within an allowable range (e.g., a range of about +/−5 to about +/−15 degrees Celsius). According to another embodiment, whether specified by the user or pre-defined, the first temperature is a temperature in a range of about 15 degrees Celsius to about 35 degrees Celsius, and the second temperature is in a range of about 10 degrees Celsius to about 20 degrees Celsius. Absolute temperatures and/or temperature differences that are greater than or less than the above given example values and ranges may be used, as well.

In addition to enabling a user to specify temperatures, the user interface may enable the user to specify one of multiple test modes that may be supported by the system, in an embodiment. For example, the system may support a first test mode in which one of the authentication temperatures is an ambient temperature (e.g., either the "first temperature" or the "second temperature," described below, is an ambient temperature). Alternatively, the system may support a second test mode in which all of the authentication temperatures correspond to temperatures that are achieved by the system through active control of the temperature adjustment element (e.g., temperature adjustment element 314). In yet another embodiment, the system may support test modes of varying accuracy. For example, a relatively low-accuracy test mode may base an authentication determination on emissions detected at two temperatures, whereas a relatively high-accuracy test mode may base an authentication determination on emissions detected at more than two temperatures. According to an embodiment, the user may specify such a test mode.

In still other embodiments, the user interface may enable the user to specify other parameters related to the authentication process (e.g., temperature adjustment durations, excitation provision durations, excitation energy wavelengths and/or intensities, excitation difference authentication thresholds, and so on), where the specified values for each of the configurable parameters is stored in data storage (e.g., data storage 318). In an alternate embodiment, the system may not support user configuration of authentication temperatures and/or other parameters and/or test mode selection. In such an embodiment, the authentication parameters and other parameters may be pre-defined and stored in data storage (e.g., data storage 318), and/or a single test mode may be implemented in the system.

For purposes of explanation, the embodiment discussed below describes a test mode in which an authentication determination is made based on emissions detected at two temperatures (e.g., the "first temperature" and the "second temperature," described below). Further, the embodiment discussed below describes an authentication process in which the first and second temperatures are non-ambient, absolute temperatures, and in which the system achieves the first and second temperature through active control of a temperature adjustment element (e.g., temperature adjustment element 314). Variations of the below-described embodiment that result in the performance of other embodiments of authentication processes are intended to be within the scope of the disclosure.

To initiate authentication of an article (e.g., article 350), the article is "received" by the system, in block 404. For example, the system may receive an article to be authenticated when the user inserts the article into a chamber of the system (e.g., chamber 334) or when the user otherwise brings a portion of the article (e.g., portion 360 and/or authentication feature 358) at which a thermographic phosphor of an embodiment should be present (in an authentic article) into thermal contact with the system's temperature adjustment element (e.g., temperature adjustment element 314) and in proximity to the excitation window (e.g., window 340) with an air gap between the article and the excitation window. In an alternate embodiment, the system may include an automatic routing component that automatically routes the article into a position in which it is proximate to the temperature adjustment element and the excitation window. Either way, the system may be configured to detect the presence of the article and may automatically initiate the authentication process described below, or the user may initiate the authentication process via the user interface (e.g., by pressing a start button or providing a similar input), in various embodiments.

According to an embodiment, the authentication process includes a sequence of article temperature adjustment, excitation energy provision, and emissions detection steps (e.g., blocks 406, 408, 410, 412, 414, 416), followed by an analysis of the detected emissions (e.g., blocks 418, 420), if any, to determine whether emissions from the article at different temperatures is sufficiently different to indicate an authentic article. Control of the various steps of the authentication method and the emissions analysis are performed by a processing system (e.g., processing system 302), according to an embodiment. More specifically, the processing system controls the timing of the execution of the various steps by providing control signals to various system components (e.g., temperature controller 312, excitation energy generator 304, and emitted radiation detector 306), which cause the various system components to initiate and perform the various steps.

To authenticate an article that has been received by the system, in block 406, the temperature adjustment element (e.g., temperature adjustment element 316) is actively controlled to achieve a first temperature, in an embodiment. For example, the processing system may retrieve the first temperature from data storage (e.g., data storage 318), and the processing system may send a control signal to a temperature controller (e.g., temperature controller 312), which indicates the first temperature. In response to receiving the control signal, the temperature controller may control the temperature adjustment element (e.g., temperature adjustment element 314) to achieve the first temperature. For example, in an embodiment in which the temperature adjustment element is a resistive type of heater, the temperature controller may cause an amount of energy to be provided to the resistive element(s) of the heater (e.g., by charging a capacitor or providing current for a pre-determined period), which is sufficient to raise the temperature of the article to a desired temperature or by a desired temperature difference. Alternatively, in an embodiment in which the temperature adjustment element is TEC, the temperature controller may provide current through the TEC, where the polarity of the current depends on whether the TEC is being used to remove heat from the article-facing surface of the TEC (e.g., to cool the portion 360 of the article 350 in proximity to the article-facing surface of the TEC) or whether the TEC is being used to provide heat to the article-facing surface of the TEC (e.g., to heat the portion 360 of the article 350 in proximity to the article-facing surface of the TEC).

According to an embodiment in which the system includes a temperature sensor (e.g., temperature sensor 316) proximate to the temperature adjustment element, the temperature sensor may sense the temperature (e.g., the temperature of the portion 360 of the article 350, the temperature of a resistive element of a resistive type of heater, or the temperature of the article-facing surface of the TEC), and may continually, periodically, or occasionally provide a signal to the temperature controller indicating the current temperature that is sensed by the temperature sensor. In such an embodiment, the temperature controller may adjust its control of the temperature adjustment element, based on the difference between the current temperature and the first temperature, in order to achieve the first temperature.

In addition, the temperature controller (or the temperature sensor) may provide a signal to the processing system and/or to a temperature monitor component (not illustrated) of the user interface, if included in the system, which indicates the current temperature, in an embodiment. The temperature monitor component may display the current temperature to the user of the system, in an embodiment. In addition or alternatively, the temperature controller may send a control signal to the processing system indicating that the current temperature has reached the first temperature to within an acceptable tolerance (e.g., the current temperature "substantially equals" the first temperature). When the processing system determines that the current temperature substantially equals the first temperature (e.g., in response to receiving the signal(s) from the temperature controller and/or the temperature sensor), the processing system may proceed to the next portion of the authentication process (i.e., to block 408, described later).

According to an embodiment in which the first temperature is ambient temperature, block 406 may be replaced with an ambient temperature sensing step. Alternatively, block 406 may be excluded altogether. In the former embodiment (i.e., in which the process includes an ambient temperature sensing step), a temperature sensor (e.g., temperature sensor 316) may sense the ambient temperature (e.g., the temperature of the portion 360 of the article 350, the temperature of a resistive element of a resistive type of heater, or the temperature of the article-facing surface of the TEC), and may provide a signal indicating the ambient temperature to the temperature controller, the processing system, and/or the temperature monitor component, which indicates the sensed ambient temperature, and the sensed ambient temperature may be stored in data storage (e.g., data storage 318) as the "first temperature." When the processing system has received the sensed ambient temperature, the processing system may proceed to the next portion of the authentication process (i.e., to block 408).

In block 408, which is performed after the first temperature has been reached, the ambient temperature has been sensed, or upon the elapse of a pre-determined period of time, in various embodiments, the article is exposed to appropriate excitation energy (i.e., excitation energy within the absorption band of an authentic thermographic phosphor). For example, the processing system may send a control signal to an excitation energy generator (e.g., excitation energy generator 304), which indicates that the excitation energy generator should initiate provision of appropriate excitation energy, the wavelength of the excitation energy, and/or the duration for which the excitation energy generator should provide the excitation energy (or a start time and a stop time). In response to receiving the control signal, the excitation energy generator produces the excitation energy (e.g., excitation energy 342) according to any parameters that are specified in the control signal. For example, in embodiments in which an Er:YIG thermographic phosphor is incorporated into an authentic article, the excitation energy generator may provide excitation energy in the iron and/or erbium absorption bands. In embodiments in which other thermographic phosphors are incorporated on or within authentic articles, the excitation energy generator may provide excitation energy in whichever absorption band is appropriate for the thermographic phosphor.

The excitation energy generator provides the excitation energy for a period of time (e.g., as indicated or controlled by the processing system). At the end of that period of time, the exposure of the article to the excitation energy is discontinued, in block 410, and the system attempts to detect emitted radiation (e.g., emitted radiation 344) from the article. For example, the processing system may send a control signal to an emissions detector (e.g., emissions detector 306), which causes the emissions detector to attempt to detect emitted radiation (e.g., emitted radiation 344) emanating from a portion of the article (e.g., portion 360 of article 350) in response to emitting ions of an authentic thermographic phosphor having absorbed (either directly or indirectly) at least some of the excitation energy. For example, in embodiments in which an Er:YIG thermographic phosphor is incorporated on or within an authentic article, the emissions detector may attempt to detect emitted radiation corresponding to erbium emission in an erbium emission band (e.g., in a band between about 1460 nm and about 1660 nm). In other embodiments in which other thermographic phosphors with other emitting ions are incorporated on or within authentic articles, the emissions detector may attempt to detect emitted radiation corresponding to the other emitting ions.

As discussed previously, in an embodiment, upon discontinuation of the excitation energy, the emissions detector may digitize one or more integrated intensity values, and the emissions detector may provide signals to the processing system, which represent the one or more integrated intensities of the emitted radiation at the first temperature (e.g., the "first intensity values"). From the first intensity values provided by the emissions detector, the processing system may determine one or more emission characteristics (e.g., one or more temporal and/or spectral characteristics of the emitted radiation). For example, the processing system may determine a first decay time constant of the detected emissions.

Upon removal of the excitation energy, the intensity of any emitting ion emission decays over time, and the rate of decay for an emitting ion can be characterized by the decay time constant. For example, for a simple exponential decay in emission intensity, the decay time constant can be represented by the constant $\tau$ in the equation:

$$I(t) = I_0 e^{-t/\tau}, \qquad \text{(Equation 1)}$$

where t denotes time, I(t) denotes the emission intensity at time t, and $I_0$ denotes the emission intensity at t=0 (e.g., t=0 may correspond to the instant when the provision of excitation energy is discontinued). Although the emission intensity for some thermographic phosphors may decay according to the above, simple exponential formula, the emission intensity for other thermographic phosphors may be affected by multiple exponential decays (e.g., when multiple mechanisms affecting the decay are present). In some cases, a thermographic phosphor may not exhibit a simple single exponential decay, especially when energy transfer is part of the mechanism.

According to an embodiment, the processing system correlates the first temperature with the temporal and/or spectral characteristics of the emitted radiation at the first temperature. For example, the processing system may store (e.g., in data storage 318) the intensity values and/or the first decay time constant in association with the first temperature.

Blocks 406, 408, and 410 are then substantially repeated (i.e., as blocks 412, 414, and 416) for a second temperature. More specifically, in block 412, the temperature adjustment element is actively controlled to achieve a second temperature, in an embodiment. For example, the processing system may retrieve the second temperature from data storage (e.g., data storage 318), and the processing system may send a control signal to the temperature controller, which indicates the second temperature. In response to receiving the control signal, the temperature controller may control the temperature adjustment element (e.g., temperature adjustment element 314) to achieve the second temperature, as previously described. According to an embodiment, the second temperature is a temperature that is lower than the first temperature (e.g., by a temperature difference in a range of about −5 to about −15 degrees Celsius, or some other difference). In an alternate embodiment, the second temperature is a temperature that is higher than the first temperature (e.g., by a temperature difference in a range of about 5 to about 15 degrees Celsius, or some other difference).

As also described previously, the temperature controller (or the temperature sensor) may provide a signal to the processing system and/or to a temperature monitor component (not illustrated) of the user interface, if included in the system, which indicates the current temperature, in an embodiment. In addition or alternatively, the temperature controller may send a control signal to the processing system indicating that the current temperature has reached the second temperature to within an acceptable tolerance (e.g., the current temperature "substantially equals" the second temperature). When the processing system determines that the current temperature substantially equals the second temperature (e.g., in response to receiving the signal(s) from the temperature controller and/or the temperature sensor), the processing system may proceed to the next portion of the authentication process (i.e., to block 414, described later).

According to an embodiment in which the second temperature is ambient temperature, block 412 may be replaced with a temperature normalization step. For example, to allow the article to return to an ambient temperature, the temperature controller may cease actively controlling the temperature adjustment element, and the system may wait a period of time for the temperature of the article to normalize to or toward an ambient temperature.

At the end of the period of time, the temperature sensor may sense the current temperature (e.g., the temperature of the portion 360 of the article 350, the temperature of a resistive element of the resistive type of heater, or the temperature of the article-facing surface of the TEC), and may provide a signal indicating the current temperature to the temperature controller, the processing system, and/or the temperature monitor component. This "sensed" ambient temperature may be stored in data storage (e.g., data storage 318) as the "second temperature." The processing system may then proceed to the next portion of the authentication process (i.e., to block 414).

In block 414, which is performed after the second temperature has been reached, the ambient temperature has been sensed, or upon the elapse of a pre-determined period of time, in various embodiments, the article again is exposed to appropriate excitation energy (i.e., excitation energy within the absorption band of an authentic thermographic phosphor), as described previously in conjunction with block 408. The excitation energy generator provides the excitation energy for a period of time (e.g., as indicated or controlled by the processing system). At the end of that period of time, the exposure of the article to the excitation energy is discontinued, in block 416, and the system attempts to detect emitted radiation (e.g., emitted radiation 344) from the article, as also described previously in conjunction with block 410. According to an embodiment, the excitation energy generator provides the excitation energy using the same parameters as were used to provide the excitation energy in conjunction with performing the first excitation energy exposure (i.e., for the same period of time and at the same wavelength as in step 408).

As discussed previously, in an embodiment, upon discontinuation of the excitation energy, the emissions detector may digitize one or more integrated intensity values, and the emissions detector may provide signals to the processing system, which represent the integrated intensity (or intensities) of the emitted radiation at the second temperature (e.g., the "second intensity values"). From the second intensity value(s) provided by the emissions detector, the processing system again may determine one or more emission characteristics (e.g., one or more temporal and/or spectral characteristics of the emitted radiation). For example, the processing system may determine a second decay time constant of the detected emissions. According to an embodiment, the processing system correlates the second temperature with the temporal and/or spectral characteristics of the emitted radiation at the second temperature. For example, the processing system may store (e.g., in data storage 318) the second intensity values and/or the second decay time constant in association with the second temperature.

In block 418, the processing system then analyzes the temporal and/or spectral characteristics of the first and second emissions in order to determine whether or not the temporal and/or spectral characteristics of any detected radiation correspond to the temporal and/or spectral characteristics of an authentic article. According to an embodiment, the processing system compares the temporal and/or spectral characteristics of the first and second emissions. For example, to compare the spectral characteristics of the first and second emissions, the processing system may determine a ratio of the first and second integrated intensities at the first and second temperatures, which are measured when the excitation energy associated with each measurement is discontinued (i.e., t=0) or at a given time after discontinuation of the excitation energy as follows:

$$R_I = I(T_1)/I(T_2), \qquad \text{(Equation 2)}$$

where $R_I$ is the intensity ratio, $I(T_1)$ is the intensity measured at the first temperature, $T_1$, at a given time with respect to discontinuation of the excitation energy associated with the first intensity measurement, and $I(T_2)$ is the intensity measured at the second temperature, $T_2$, at the same given time with respect to discontinuation of the excitation energy associated with the second intensity measurement.

Conversely, in embodiments in which multiple measurements of integrated intensities (at different times with respect to discontinuation of the excitation energy) are made at a first temperature and at a second temperature, the temporal characteristics of the first and second emissions may use the multiple integrated intensity values as variables in a mathematical equation in order to calculate a decay time constant corresponding to emissions produced at each of the temperatures. A magnitude of a difference between the first and second decay time constants may then be determined For example, the processing system may determine a first decay time constant for emissions at the first temperature (Equation 3a, below), determine a second decay time constant for emissions at the second temperature (Equation 3b, below), and determine a difference between the first and second decay time constants (Equation 3c, below) as follows:

$$\tau_{T1} = -(t_2-t_1)/\ln(I(T_1(t_1)/I(T_1(t_2))), \qquad \text{(Equation 3a)}$$

$$\tau_{T2} = -(t_2-t_1)/\ln(I(T_2(t_1)/I(T_2(t_2))), \qquad \text{(Equation 3b)}$$

$$\Delta\tau = \tau_{T1} - \tau_{T2}, \qquad \text{(Equation 3c)}$$

where $\tau_{T1}$ is a value representing a first decay time constant at the first temperature, $T_1$, $\tau_{T2}$ is a value representing a second decay time constant at the second temperature, $T_2$, and $\Delta\tau$ is the difference between the first and second decay time constants.

Alternatively, to compare the spectral characteristics of the first and second emissions, the processing system may determine a difference between first and second intensity values as follows:

$$\Delta_I = I(T_1) - I(T_2), \qquad \text{(Equation 4)}$$

where $\Delta_I$ is the intensity difference. Conversely, to compare the temporal characteristics of the first and second emissions, the processing system may determine a ratio of the first and second decay time constants at the first and second temperatures as follows:

$$R_\tau = \tau_{T1}/\tau_{T2}, \qquad \text{(Equation 5)}$$

where $R_\tau$ is the ratio of the first and second decay time constants.

In other embodiments, other mathematical equations may be used to indicate differences in the temporal and/or spectral characteristics of the first and second emissions. In addition, in embodiments in which three or more iterations of the temperature adjustment, excitation energy exposure, and emitted radiation detection processes are performed, the mathematical equations may take into account the three or more measured intensities and/or decay time constants in determining rates of change of intensity or decay time constant as a function of temperature, and those determined rates of change may be considered to indicate how temperature affects the intensity and/or decay time constant.

As discussed previously, the temporal and/or spectral characteristics of a thermographic phosphor change with temperature. Accordingly, for an article with an authentic thermographic phosphor, the system anticipates that the temporal and/or spectral characteristics of any emissions detected from the article will be different at the first and second temperatures. According to an embodiment, when the temporal and/ or spectral characteristics are "sufficiently different," the article may be considered to be authentic. Conversely, when the temporal and/or spectral characteristics are not "sufficiently different," the article may be considered to be unauthentic.

In block 420, the processing system determines whether there is a detectable difference in the temporal and/or spectral characteristics of the first and second emissions. For example, the processing system may determine whether the temporal and/or spectral characteristics of the first and second emissions are "sufficiently different" to indicate an authentic article. This determination may include comparing one or more the ratios and/or differences that reflect intensities and/or decay time constants (e.g., as calculated in Equations 2-5, above) with corresponding authentication thresholds (e.g., "intensity-related authentication thresholds" and "decay time constant related authentication thresholds," respectively).

With respect to decay time constant related authentication thresholds, and according to an embodiment, the processing system determines that the temporal characteristics are sufficiently different when the calculations that correspond to decay time constants (e.g., Equations 3 and 5, above) indicate that the first and second decay time constants are at least 5 percent different from each other for each 10 degree Celsius difference between the first and second temperatures (e.g., the decay time constant related authentication threshold is either about 1.05 or about 0.95 for a 10 degree Celsius difference). According to another embodiment, the processing system determines that the temporal characteristics are sufficiently different when the calculations that correspond to decay time constants indicate that the first and second decay time constants are at least 10 percent different from each other for each 10 degree Celsius difference between the first and second temperatures (e.g., the decay time constant related authentication threshold is either about 1.1 or about 0.9 for a 10 degree Celsius difference). According to yet another embodiment, the processing system determines that the temporal characteristics are sufficiently different when the calculations that correspond to decay time constants indicate that the first and second decay time constants are at least 20 percent different from each other for each 10 degree Celsius difference between the first and second temperatures (e.g., the decay time constant related authentication threshold is either about 1.2 or about 0.8 for a 10 degree Celsius difference). According to yet another embodiment, the processing system determines that the temporal characteristics are sufficiently different when the calculations that correspond to decay time constants indicate that the first and second decay time constants are at least thirty percent different from each other for each 10 degree Celsius difference between the first and second temperatures (e.g., the decay time constant related authentication threshold is either about 1.3 or about 0.7 for a 10 degree Celsius difference). Proportionally smaller or larger decay time constant related authentication thresholds could be implemented for smaller or larger differences, respectively, between the first and second temperatures.

According to yet another embodiment, the processing system may determine whether or not the temporal characteristics are sufficiently different based on the slope direction and magnitude of the temperature (e.g., x-axis) to decay time constant (e.g., y-axis) curve. For example, the processing system may determine that the temporal characteristics are sufficiently different when the decay time constant corresponding to the higher temperature (i.e., either the first or second temperature) is at least a pre-defined percentage lower than the decay time constant corresponding to the lower temperature (i.e., the other of the first or second temperature). In other words, the processing system determines that the temporal characteristics are sufficiently different when a slope of the temperature to decay time constant curve is negative, and has a sufficient magnitude (e.g., a magnitude of at least −0.1 milliseconds per degree Celsius, or some other magnitude).

With respect to intensity related authentication thresholds, and according to another embodiment, the processing system determines that the spectral characteristics are sufficiently different when the ratio of or difference between the first and second intensities (e.g., Equations 2 and 4, above) indicates that the first and second intensities are at least 10 percent different from each other for each 10 degree Celsius difference between the first and second temperatures (e.g., the intensity related authentication threshold is either about 1.1 or about 0.9 for a 10 degree Celsius difference). According to another embodiment, the processing system determines that the spectral characteristics are sufficiently different when the ratio of, or difference between, the first and second intensities indicates that the first and second intensities are at least twenty percent different from each other for each 10 degree Celsius difference between the first and second temperatures (e.g., the intensity related authentication threshold is either about 1.2 or about 0.8 for a 10 degree Celsius difference). According to yet another embodiment, the processing system determines that the spectral characteristics are sufficiently different when the ratio of, or difference between, the first and second intensities indicates that the first and second intensities are at least thirty percent different from each other for each 10 degree Celsius difference between the first and second temperatures (e.g., the intensity related authentication threshold is either about 1.3 or about 0.7 for a 10 degree Celsius difference). Proportionally smaller or larger intensity related authentication thresholds could be implemented for smaller or larger differences, respectively, between the first and second temperatures.

Figure 5:
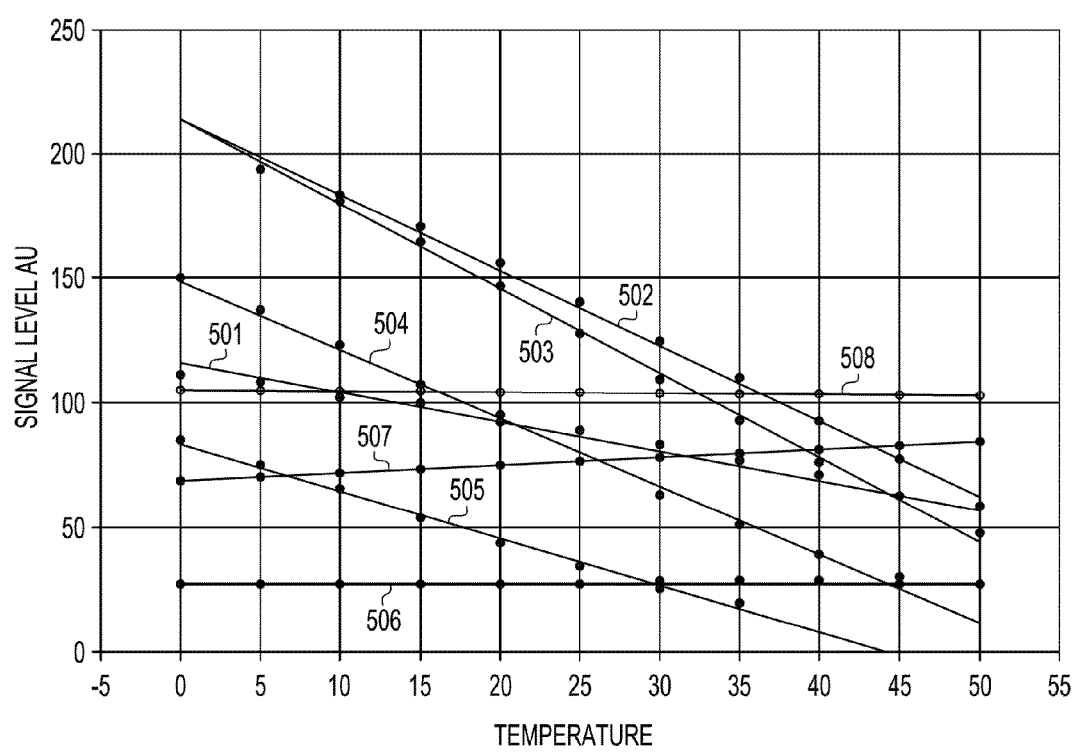
FIG. 5 is a graph illustrating emission intensities of multiple thermographic phosphor samples with respect to temperature, according to several example embodiments.
Figure 6:
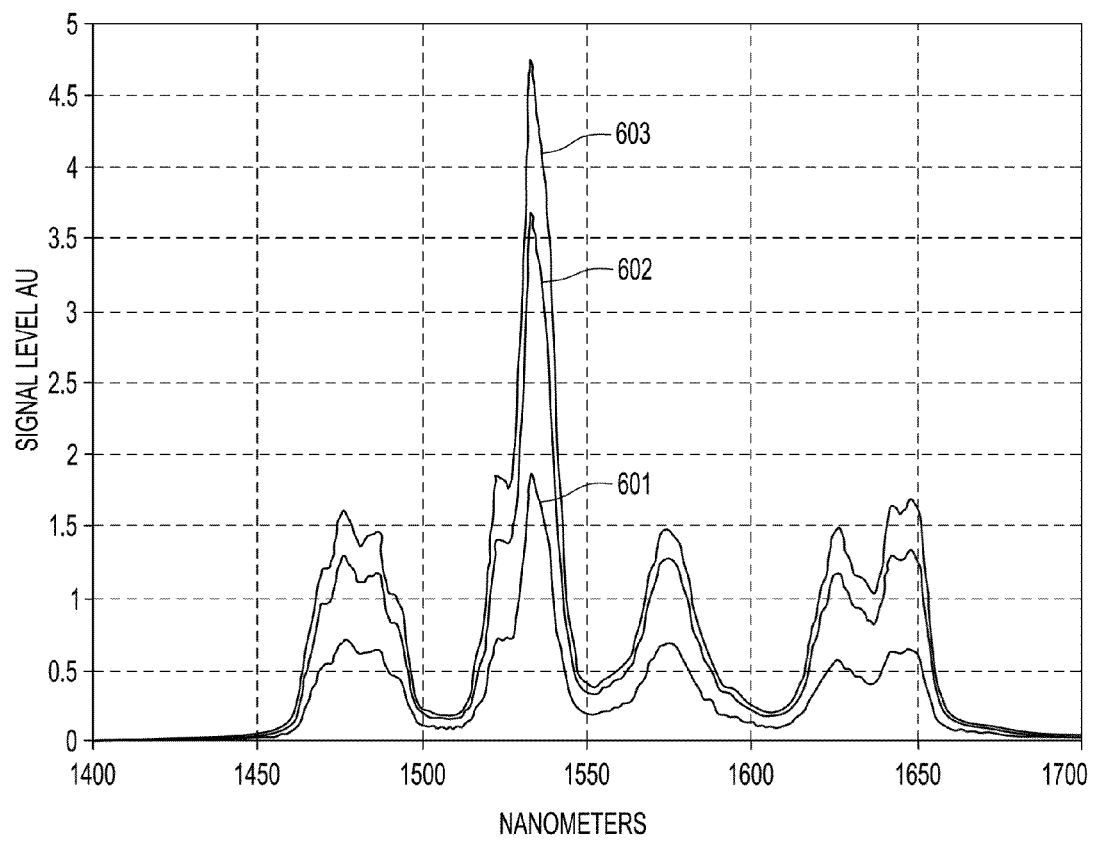
FIG. 6 illustrates the spectral emission characteristics of a thermographic phosphor sample with respect to temperature, according to an example embodiment.
Figure 7:
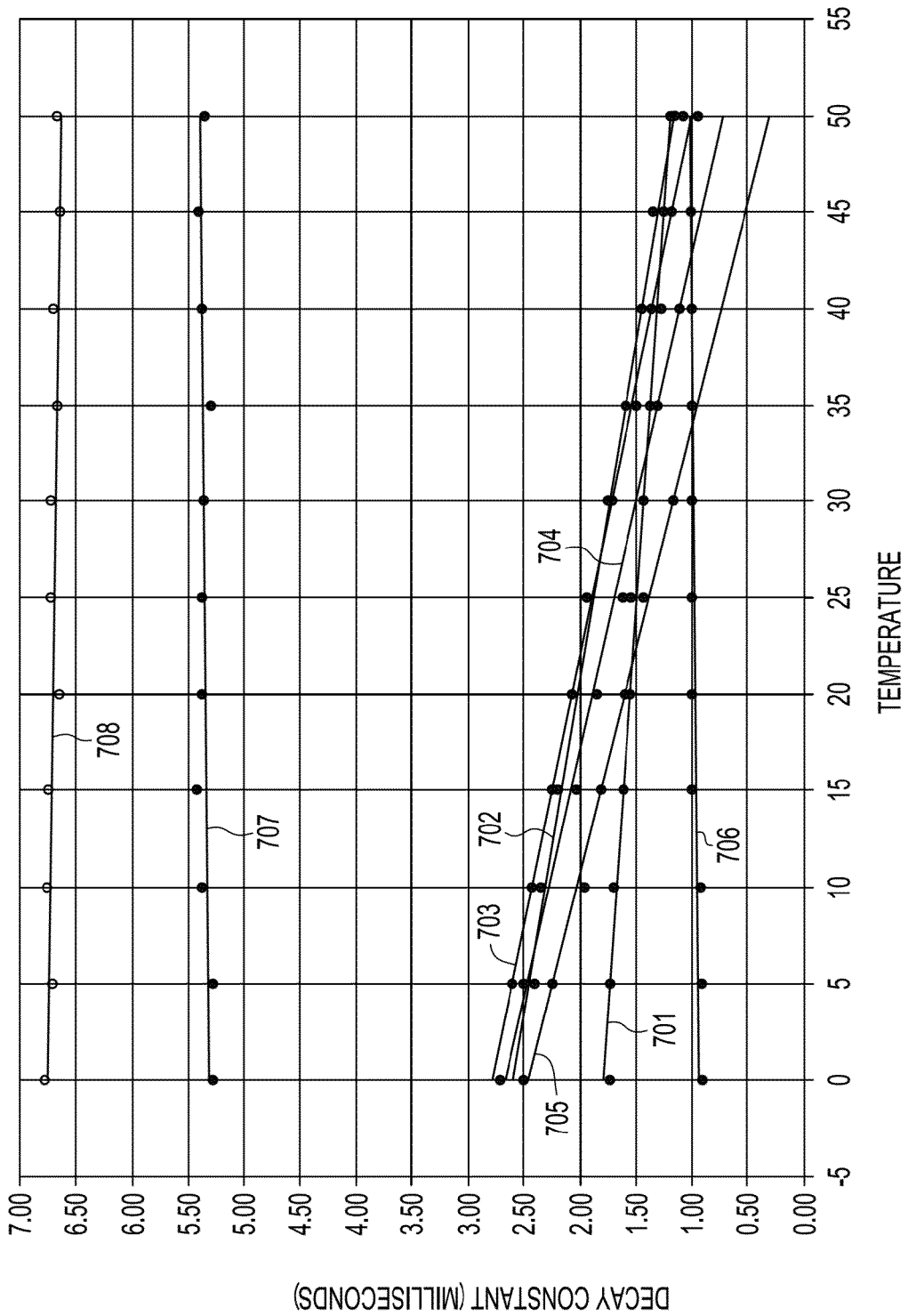
FIG. 7 is a graph illustrating decay time constants of multiple thermographic phosphor samples with respect to temperature, according to several example embodiments.

According to yet another embodiment, the processing system may determine whether or not the spectral characteristics are sufficiently different based on the slope direction and magnitude of the temperature (e.g., x-axis) to intensity (e.g., y-axis) curve. For example, some embodiments of thermographic phosphors (e.g., embodiments of Er:YIG) exhibit an inversely proportional relationship between temperature and both decay time constant and intensity (e.g., as shown in FIGS. 5-7). Accordingly, for those thermographic phosphor embodiments, when the first temperature is greater than the second temperature, the first decay time constant and the first intensity would be less than the second decay time constant and the second intensity in an authentic thermographic phosphor. When performing authentication for such a thermographic phosphor, the processing system may determine that the spectral characteristics are sufficiently different when the intensity corresponding to the higher temperature is at least a pre-defined percentage lower than the intensity corresponding to the lower temperature. Other embodiments of thermographic phosphors may exhibit a directly proportional relationship between temperature and intensity (e.g., the temperature vs. intensity relationship for embodiments of Cr:Er:YGG as represented by trace 507, FIG. 5). Accordingly, for those thermographic phosphor embodiments, when the first temperature is greater than the second temperature, the first intensity would be greater than the second intensity in an authentic thermographic phosphor. When performing authentication for such a thermographic phosphor, the processing system may determine that the spectral characteristics are sufficiently different when the intensity corresponding to the higher temperature is at least a pre-defined percentage greater than the intensity corresponding to the lower temperature. Either way, the processing system may determine that the spectral characteristics are sufficiently different when a slope of the temperature to intensity curve falls within expected pre-determined parameters (e.g., the slope has a sign that corresponds to the expected sign for an authentic thermographic phosphor, and the slope has a sufficient magnitude (e.g., a magnitude of at least 0.1 arbitrary unit per degree Celsius, or some other magnitude)).

In yet another embodiment, rather than calculating comparison values (e.g., ratios or differences) between the intensities, the processing system may analyze the temporal and/or spectral characteristics of the first and second emissions separately, to determine whether the emissions at each temperature had temporal and/or spectral characteristics that fall within pre-determined, different ranges (i.e., non-overlapping ranges) that correspond to an authentic thermographic phosphor.

When the processing system determines, in block 420, that the temporal and/or spectral characteristics of the emissions at the first and second temperatures are sufficiently different (or fall within appropriate but different ranges), the processing system may identify the article as being authentic, in block 422. For example, the processing system may take some action associated with identifying the article as an authentic article. For example, the processing system may send a signal associated with authenticity to the user interface (e.g., user interface 320), which causes the user interface to produce a user-perceptible indication of authenticity (e.g., a displayed indicia, a light, a sound, and so on). Alternatively, the processing system may cause a routing component of the system (not illustrated) to route the article toward a route or bin assigned for authentic articles.

Conversely, when the processing system determines that the temporal and/or spectral characteristics of the emissions at the first and second temperatures is not sufficiently different, the processing system may identify the article as being unauthentic, in block 424. For example, when the temporal and/or spectral properties of the detected radiation do not correspond with an authentic article, the processing system may take some action associated with identifying the article as an unauthentic article. For example, the processing system may send a signal associated with unauthenticity to the user interface, which causes the user interface to produce a user-perceptible indication of unauthenticity (e.g., a displayed indicia, a light, a sound, and so on). Alternatively, the processing system may cause a routing component of the system (not illustrated) to route the article toward a route or bin assigned for unauthentic articles.

The embodiments discussed above indicate that the system makes an authentication decision based on a determination of whether or not the system detects that an article includes an authentic thermographic phosphor. Other system and method embodiments also may use additional considerations in making an authentication decision. For example but not by way of limitation, another embodiment of an article may include one or more additional security features and/or one or more additional thermographic and/or non-thermographic phosphor materials (e.g., one or more "reference" phosphor materials). Accordingly, other system embodiments may attempt to determine whether an article presented for authentication includes the additional security feature(s) and/or the additional phosphor(s). When the system determines that the article includes all expected security features, the system may determine that the article is authentic. Conversely, when the system determines that the article does not include one or more of the expected security features, the system may determine that the article is unauthentic.

FIGS. 5-7 include graphs depicting emission characteristics of various embodiments of thermographic phosphors (and other phosphors) incorporated into articles. For example, FIG. 5 is a graph illustrating emission intensities of multiple thermographic phosphor and other (non-thermographic) phosphor samples with respect to temperature, according to several example embodiments. To generate the results depicted in FIG. 5, particles of various thermographic phosphor and other phosphor samples were included in inks printed on paper handsheet article substrates. More particularly, ink materials were created that included an ink base and various Er:YIG samples, according to several embodiments. In addition, for comparison purposes, additional ink materials were created that included an ink base and an Er:YOS (yttrium oxysulfide) sample, a Cr:Er:YGG (yttrium gallium garnet) sample, and an Er:YAG (yttrium aluminum garnet) sample. Each of the ink materials was printed on a surface of a paper handsheet article substrate.

For example, to produce a sample used to generate trace 501, a first ink material was created that comprised Er:YIG (with the Er at 32 percent in a YIG host lattice material). To produce a sample used to generate trace 502, a second ink material was created that comprised Er:YIG (with the Er at 12 percent in a YIG host lattice material). To produce a sample used to generate trace 503, a third ink material was created that comprised Er:YIG (with the Er at 6 percent in a YIG host lattice material). To produce a sample used to generate trace 504, a fourth ink material was created that comprised Er:YIG (with the Er at 3 percent in a YIG host lattice material). To produce a sample used to generate trace 505, a fifth ink material was created that comprised Er:YIG (with the Er at 1 percent in a YIG host lattice material). To produce a sample used to generate trace 506, a sixth ink material was created that comprised Er:YOS (with the Er at 20 percent in a YOS host lattice material). To produce a sample used to generate trace 507, a seventh ink material was created that comprised Cr:Er:YGG (with the Cr at 20 percent and the Er at 3 percent in a YGG host lattice material). Finally, to produce a sample used to generate trace 508, an eighth ink material was created that comprised Er:YAG (with the Er at 3 percent in a YAG host lattice material).

For samples 501 through 505, an LED was used to excite the printed feature into the iron absorption band (e.g., at about 630 nm). For sample 506, an LED was used to excite the printed feature into the Er absorption band (e.g., at about 660 nm). For sample 507, an LED was used to excite the printed feature into the chromium absorption band (e.g., at about 630 nm). Finally, for sample 508, an LED was used to excite the printed feature into the Er absorption band (e.g., at about 660 nm). For each of the samples, after discontinuing the excitation, the resulting emission intensities were detected by an authentication system at 5 degree Celsius temperature increments over a range from about 0 degrees Celsius to about 50 degrees Celsius. More particularly, the detected emissions included emissions between about 1460 nm and about 1660 nm (i.e., in an erbium emission band) for each of the samples.

As shown in FIG. 5, the Er:YIG phosphors (i.e., samples 501-505) exhibited highly thermographic properties, in that the intensity of the erbium emissions decreased significantly as the temperature increased. Said another way, the intensity of the erbium emissions increased significantly as the temperature decreased. Accordingly, the intensity of the erbium emissions in the Er:YIG phosphors was inversely proportional to the temperature of samples 501-505. Conversely, the Er:YOS and Er:YAG phosphors (i.e., samples 506 and 508) exhibited a substantially flat intensity to temperature profile. Finally, the Cr:Er:YGG phosphor (i.e., sample 507) did exhibit some thermographic properties, in that the intensity of the erbium emissions increased slightly as the temperature increased (i.e., the intensity of the erbium emissions in the Cr:Er:YGG phosphor was directly proportional to the temperature of sample 507). However, the slope of the temperature to intensity curve for the Cr:Er:YGG phosphor (i.e., sample 507) has a significantly lower magnitude than the slope of the temperature to intensity curves for the Er:YIG phosphors (i.e., samples 501-505). Accordingly, the Er:YIG phosphors may be more readily detectable (or their absence may be more readily apparent) than the Cr:Er:YGG phosphor.

As a further illustration, FIG. 6 depicts the spectral emission characteristics of a thermographic phosphor sample with respect to temperature, according to an example embodiment. More specifically, FIG. 6 illustrates the spectral emission characteristics, at multiple temperatures, of an Er:YIG sample (with the Er at 3 percent in a YIG host lattice material), which was included in an ink material that was printed on a surface of a paper handsheet article substrate. Trace 601 corresponds to the intensity of emissions in an erbium emission band spanning from 1460 nm to 1660 nm when the article substrate was at a temperature of about 33.0 degrees Celsius. Trace 602 corresponds to the intensity of emissions in the erbium emission band when the article substrate was at a temperature of about 22.3 degrees Celsius. Finally, trace 603 corresponds to the intensity of emissions in the erbium emission band when the article substrate was at a temperature of about 11.6 degrees Celsius. Again, the Er:YIG phosphor sample exhibited highly thermographic properties, in that the intensity of emissions at a relatively high temperature (i.e., trace 601) is significantly lower than the intensity of emissions at a relatively low temperature (i.e., trace 603).

FIG. 7 is a graph illustrating decay time constants of multiple thermographic phosphor samples with respect to temperature, according to several example embodiments. Traces 701-708 were produced using the same samples as were used to produce corresponding traces 501-508 of FIG. 5. More particularly, trace 701 corresponds to a sample that included Er:YIG (with the Er at 32 percent in a YIG host lattice material) in a first ink material. Trace 702 corresponds to a sample that included Er:YIG (with the Er at 12 percent in a YIG host lattice material) in a second ink material. Trace 703 corresponds to a sample that included Er:YIG (with the Er at 6 percent in a YIG host lattice material) in a third ink material. Trace 704 corresponds to a sample that included Er:YIG (with the Er at 3 percent in a YIG host lattice material) in a fourth ink material. Trace 705 corresponds to a sample that included Er:YIG (with the Er at 1 percent in a YIG host lattice material) in a fifth ink material. Trace 706 corresponds to a sample that included Er:YOS (with the Er at 20 percent in a YOS host lattice material) in a sixth ink material. Trace 707 corresponds to a sample that included Cr:Er:YGG (with the Cr at 20 percent and the Er at 3 percent in a YGG host lattice material) in a seventh ink material. Finally, trace 708 corresponds to a sample that included Er:YAG (with the Er at 3 percent in a YAG host lattice material) in an eighth ink material.

For samples 701 through 705, an LED was used to excite the printed feature into the iron absorption band (e.g., at about 630 nm). For sample 706, an LED was used to excite the printed feature into the Er absorption band (e.g., at about 660 nm). For sample 707, an LED was used to excite the printed feature into the chromium absorption band (e.g., at about 630 nm). Finally, for sample 708, an LED was used to excite the printed feature into the Er absorption band (e.g., at about 660 nm). For each of the samples, after discontinuing the excitation, the resulting decay time constants were calculated by an authentication system at 5 degree Celsius temperature increments over a range from about 0 degrees Celsius to about 50 degrees Celsius. More particularly, each decay time constant was calculated based on multiple, time-incremental measurements of the intensities of detected emissions between about 1460 nm and about 1660 nm (i.e., in an erbium emission band) for each of the samples at each of the temperatures.

As shown in FIG. 7, the Er:YIG phosphors (i.e., samples 701-705) exhibited highly thermographic properties, in that the decay time constants of the erbium emissions decreased significantly as the temperature increased (or the decay time constants of the erbium emissions increased significantly as the temperature decreased). Accordingly, the decay time constants of the erbium emissions in the Er:YIG phosphors was inversely proportional to the temperature of samples 701-705. Conversely, the Er:YOS, Cr:Er:YGG, and Er:YAG phosphors (i.e., samples 706-708) exhibited a substantially flat decay time constant to temperature profile.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for identifying a luminescent material incorporated on or within an article, the method comprising the steps of:
    selectively exposing the article to excitation energy in an absorption band of the luminescent material;
    detecting first emission characteristics of first emitted radiation from the article within an emission band of the luminescent material when the article has a first temperature;
    detecting second emission characteristics of second emitted radiation from the article within the emission band when the article has a second temperature that is different from the first temperature; and
    determining whether the first emission characteristics are sufficiently different from the second emission characteristics, wherein determining whether the first emission characteristics are sufficiently different from the second emission characteristics comprises determining whether a first intensity of the first emitted radiation is at least about 1 percent different from a second intensity of the second emitted radiation for each degree of difference between the first and second temperatures.

2. The method of claim 1, wherein selectively exposing the article to the excitation energy comprises:
    first exposing a portion of the article to the excitation energy during a first period of time that coincides with the portion of the article having the first temperature;
    discontinuing the first exposing prior to detecting the first emission characteristics;
    second exposing the portion of the article to the excitation energy during a second period of time that coincides with the portion of the article having the second temperature; and discontinuing the second exposing prior to detecting the second emission characteristics.

3. The method of claim 1, wherein at least one of the first temperature and the second temperature is a temperature that is achieved through active control of a temperature adjustment element, and wherein the method further comprises:
actively controlling the temperature adjustment element to achieve the at least one of the first temperature or the second temperature.

4. The method of claim 3, wherein both the first temperature and the second temperature are temperatures that are achieved through active control of the temperature adjustment element, and wherein actively controlling the temperature adjustment element comprises:
prior to detecting the first emission characteristics, actively controlling the temperature adjustment element to achieve the first temperature; and
after detecting the first emission characteristics but prior to detecting the second emission characteristics, actively controlling the temperature adjustment element to achieve the second temperature.

5. The method of claim 3, wherein one of the first temperature or the second temperature is achieved through active control of the temperature adjustment element, and another one of the first temperature or the second temperature is ambient temperature, and wherein the method further comprises:
sensing the ambient temperature.

6. The method of claim 1, wherein the first temperature and the second temperature are different from each other by a temperature difference in a range of about +/−5 degrees Celsius to about +/−15 degrees Celsius.

7. The method of claim 1, wherein detecting the first emissions and detecting the second emissions comprises sequentially detecting emissions from a same portion of the article.

8. The method of claim 1, wherein determining whether the first emission characteristics are sufficiently different from the second emission characteristics comprises determining whether intensities of the first and second emitted radiation exhibit an inversely proportional relationship to temperature.

9. The method of claim 1, wherein determining whether the first emission characteristics are sufficiently different from the second emission characteristics comprises determining whether decay time constants for the first and second emitted radiation exhibit an inversely proportional relationship to temperature.

10. The method of claim 1, wherein the absorption band is an absorption band of iron, and wherein the emission band is an emission band of erbium.

11. The method of claim 1, further comprising:
when the first emission characteristics are not sufficiently different from the second emission characteristics, designating the article as being not authentic; and
when the first emission characteristics are sufficiently different from the second emission characteristics, designating the article as being authentic.

12. A method for identifying a luminescent material incorporated on or within an article, the method comprising the steps of:
selectively exposing the article to excitation energy in an absorption band of the luminescent material;
detecting first emission characteristics of first emitted radiation from the article within an emission band of the luminescent material when the article has a first temperature;
detecting second emission characteristics of second emitted radiation from the article within the emission band when the article has a second temperature that is different from the first temperature; and
determining whether the first emission characteristics are sufficiently different from the second emission characteristics, wherein determining whether the first emission characteristics are sufficiently different from the second emission characteristics comprises determining whether a first decay time constant of the first emitted radiation is at least about 1 percent different from a second decay time constant of the second emitted radiation for each degree of difference between the first and second temperatures.

* * * * *